(12) United States Patent
Backman et al.

(10) Patent No.: US 7,652,772 B2
(45) Date of Patent: Jan. 26, 2010

(54) SYSTEMS, METHODS, AND APPARATUSES OF LOW-COHERENCE ENHANCED BACKSCATTERING SPECTROSCOPY

(75) Inventors: Vadim Backman, Chicago, IL (US); Hemant Roy, Highland Park, IL (US); Young Kim, West Lafayette, IN (US); Yang Liu, Somerset, NJ (US); Vladimir Turzhitsky, Evanston, IL (US); Jeremy Rogers, Chicago, IL (US)

(73) Assignees: Northwestern University, Evanston, IL (US); NorthShore University HealthSystem, Evanston, IL (US)

( * ) Notice: Subject to any disclaimer, the term of this patent is extended or adjusted under 35 U.S.C. 154(b) by 145 days.

(21) Appl. No.: 11/803,029

(22) Filed: May 11, 2007

(65) Prior Publication Data
US 2008/0037024 A1    Feb. 14, 2008

Related U.S. Application Data

(60) Provisional application No. 60/799,970, filed on May 12, 2006.

(51) Int. Cl.
*G01B 9/02* (2006.01)
(52) U.S. Cl. .................................... 356/497
(58) Field of Classification Search ................. 356/479, 356/497
See application file for complete search history.

(56) References Cited

U.S. PATENT DOCUMENTS

| | | |
|---|---|---|
| 5,037,202 A | 8/1991 | Batchelder et al. |
| 5,303,024 A | 4/1994 | Thierman |
| 5,650,847 A | 7/1997 | Maltsev et al. |
| 5,799,656 A | 9/1998 | Alfano et al. |
| 6,320,660 B1 | 11/2001 | Ju et al. |
| 6,405,070 B1 | 6/2002 | Banerjee |
| 6,639,674 B2 | 10/2003 | Sokolov et al. |
| 6,650,357 B1 | 11/2003 | Richardson |
| 6,922,583 B1 | 7/2005 | Perelman et al. |

(Continued)

OTHER PUBLICATIONS

Adam Wax, et al., "Cellular Organization and Substructure Measured Using Angle-Resolved Low-Coherence Interferometry", Biophysical Journal, Apr. 2002, pp. 2256-2264, vol. 82.

(Continued)

*Primary Examiner*—Hwa S Lee (Andrew)
(74) *Attorney, Agent, or Firm*—Paul, Hastings, Janofsky & Walker LLP

(57) ABSTRACT

Systems, methods, and apparatuses of low-coherence enhanced backscattering spectroscopy are described within this application. One embodiment includes providing incident light comprising at least one spectral component having low coherence, wherein the incident light is to be illuminated on a target object in vivo. An intensity of one or more of at least one spectral component and at least one angular component of backscattering angle of backscattered light is recorded, wherein the backscattered light is to be backscattered from illumination of the incident light on the target object and wherein the backscattering angle is an angle between incident light propagation direction and backscattered light propagation direction. The intensity of the at least one spectral component and the at least one backscattering angle of backscattered light is analyzed, to obtain one or more optical markers of the backscattered light, toward evaluating said properties.

23 Claims, 18 Drawing Sheets

U.S. PATENT DOCUMENTS

| | | | |
|---|---|---|---|
| 6,927,860 B2 * | 8/2005 | Podoleanu et al. | 356/479 |
| 7,061,622 B2 * | 6/2006 | Rollins et al. | 356/497 |
| 2003/0215846 A1 | 11/2003 | Watt et al. | |
| 2004/0189987 A1 | 9/2004 | Bondurant et al. | |
| 2005/0046821 A1 | 3/2005 | Hanson et al. | |
| 2005/0265586 A1 | 12/2005 | Rowe et al. | |
| 2007/0201033 A1 | 8/2007 | Desjardins et al. | |

OTHER PUBLICATIONS

Irving Itzkan et al., "Confocal light absorption and scattering spectroscopic microscopy monitors organelles in live cells with no exogenous labels", Proceedings of the National Academy of Sciences, Oct. 30, 2007, pp. 17255-17260, vol. 104, No. 44.

Hariharan Subramanian et al., "Nanoscale Cellular Changes in Field Carcinogenesis Detected by Partial Wave Spectroscopy", American Association for Cancer Research Journal, Jul. 1, 2009, pp. 5357-5363.

Hariharan Subramanian et al., "Optical methodology for detecting histologically unapparent nanoscale consequences of genetic alterations in biological cells", Proceedings of the National Academy of Sciences, Dec. 23, 2008, pp. 20124-20129, vol. 105, No. 51.

Hariharan Subramanian et al., "Partial-wave microscopic spectroscopy detects subwavelength refractive index fluctuations: an application to cancer diagnosis" Optics Letters, Optical Society of America, Feb. 15, 2009, pp. 518-520, vol. 34, No. 4.

Yang Liu et al., "Elastic backscattering spectroscopic microscopy", Optic Letters, Optical Society of America, Sep. 15, 2005, pp. 2445-2447, vol. 30, No. 18.

Young L. Kim et al., "Low-coherent backscattering spectroscopy for tissue characterization", Applied Optics, Jan. 20, 2005, pp. 366-377, vol. 44, No. 3.

Young L. Kim et al., "Coherent backscattering spectroscopy", Optics Letters, Optical Society of America, Aug. 15, 2004, pp. 1906-1908, vol. 29, No. 16.

Young L. Kim et al., "Low-coherence enhanced backscattering: review of principles and applications for colon cancer screening", Journal of Biomedical Optics, Jul./Aug. 2006, pp. 041125-1-041125-10, vol. 11(4).

Young L. Kim et al., "Depth-resolved low-coherence enhanced backscattering", Optics Letters, Optical Society of America, Apr. 1, 2005, pp. 741-743, vol. 30, No. 7.

Kumar, N., "Resistance fluctuation in a one-dimensional conductor with static disorder", The American Physical Society, Physical Review B, Apr. 15, 1985, pp. 5513-5515, vol. 31, No. 8.

Stephen B. Haley et al., "Wave propagation in one-dimensional disordered structures", The American Physical Society, Physical Review B, Apr. 15, 1992, pp. 8572-8584, vol. 45, No. 15.

International Preliminary Report on Patentability dated Feb. 26, 2009 from PCT/US07/017894.

International Search Report and Written Opinion dated Mar. 19, 2008 from PCT/US07/017894.

Ingle, James D. et al., Spectrochemical Analysis, Prentice-Hall Inc., 1988, ISBN 0-13-826876-2 p. 520.

Ramanujam, Nirmala, Flourescence Spectrocopy of Neoplastic and Non-Neoplastic Tissues, Neoplasma, Neoplasma Press, Inc., Jan. 2000, V. 2(102), p. 89-117.

Brownson, RC et al., Family history of cancer and risk of lung cancer in lifetime non-smokers and long-term ex-smokers, Int J. Epidemiol, Apr. 1997, vol. 26, No. 2, p. 256-263 (abstract).

International Search Report and Written Opinion dated Jul. 22, 2008 from PCT/US07/11404.

International Preliminary Report on Patentability dated Nov. 17, 2008 from PCT/US07/11404.

Wolf, P.E., Maret, G., Akkermans, E. & Maynard, R., "Optical Coherent Backscattering by Random-Media—an Experimental-Study." Journal de Physique 49, 63-75 (1988).

Yoo, K. M., Tang, G.C., and Alfano, R.R., "Coherent Backscattering of Light from Biological Tissues." Applied Optics 29, 3237-3239 (1990).

Chen, L.C., Hao, C. Y., and Chiu, Y. C., et al., "Alteration of gene expression in normal-appearing colon mucosa of APCminmice and human cancer patients." Cancer Res 64, 3694-700 (2004).

Liu, Y., Kim, Y. L., Li, X., and Backman, V. Investigation of depth selectivity of polarization gating for tissue characterization. Opt. Express, 13: 601-611, 2005.

Roy, H. K., Kim, Y. L., Liu, Y., Wali, R. K., Goldberg, M. J., Turzhitsky, V., Horwitz, J., and Backman, V. "Risk stratification of colon carcinogenesis through enhanced backscattering (EBS) spectroscopy analysis of the uninvolved colonic mucosa," Clinical Cancer Research 12(3), 961-968 (2006).

Siegel, M. P., Kim, Y. L., Roy, H., Wali, R., and Backman, V. "Assessment of Blood Supply in Superficial Tissue using Polarization Gated Elastic Light Scattering Spectroscopy," Appl Optics, accepted 45(2), 335-342 (2006).

Wali, R. K., Roy, H. K., Kim, Y. L., Liu, Y., Koetsier, J. L., Kunte, D. P., Goldberg, M. J., Turzhitsky, V., and Backman, V. "Increased Microvascular Blood Content is an Early Event in Colon Carcinogenesis," Gut 54, 654-660 (2005).

Kim, Y., Liu, Y., Wali, R. K., Roy, H. K., Goldberg, M. J., Kromine, A. K., Chen, K., and Backman, V. "Simultaneous measurement of angular and spectral properties of light scattering for characterization of tissue microarchitecture and its alteration in early precancer," IEEE J. Sel. Top. Quantum Electron. 9, 243-257 (2003).

Kim, Y. L., Pradhan, P., Subramanian, H., Liu, Y., Kim, M. H., and Backman, V. "Origin of low-coherence enhanced backscattering," Optics Letters 31(10), 1459-1461 (2006).

* cited by examiner

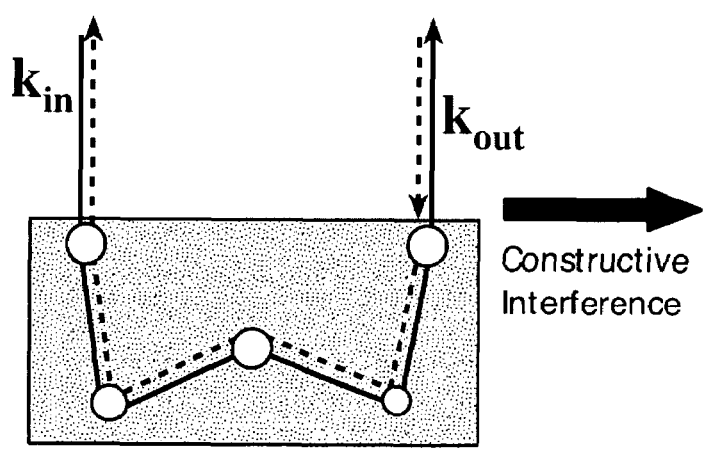 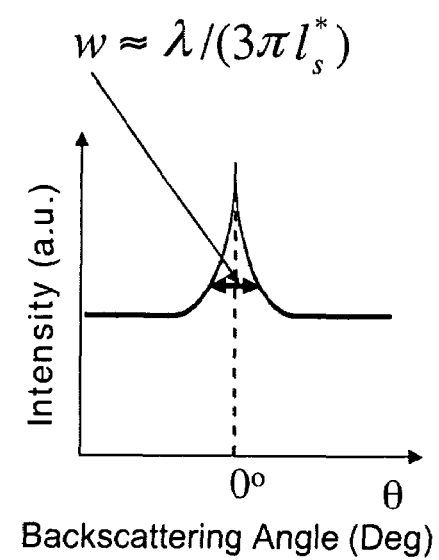
*Figure 1A*  *Figure 1B*

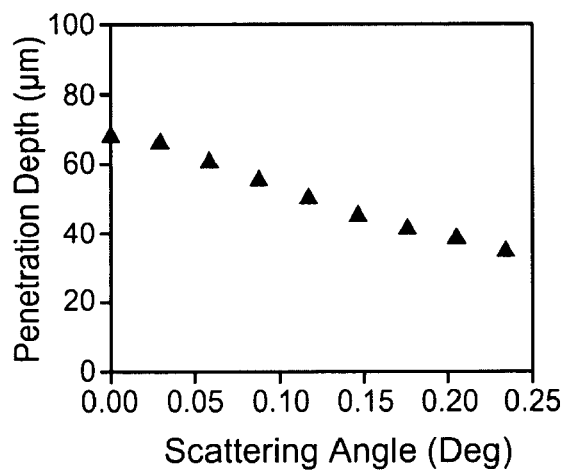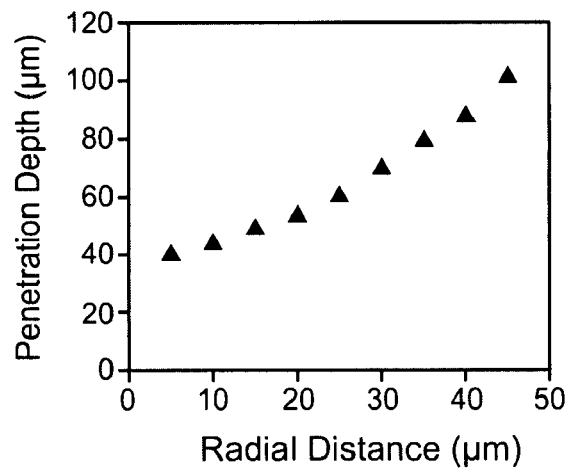
*Figure 3A*  *Figure 3B*

Fourier Transform

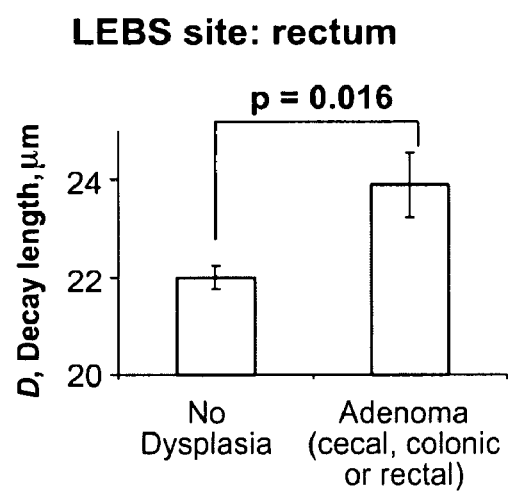 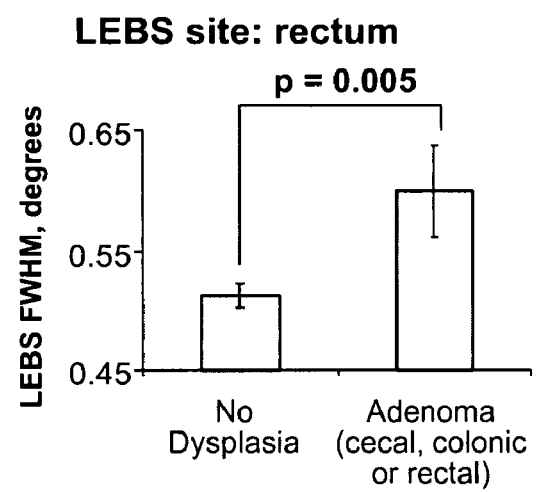
Figure 14B
Figure 14C

| | Sensitivity and specificity of LEBS markers for predicting neoplastic risk. | | | |
|---|---|---|---|---|
| | AOM-treated versus saline-treated rat (%) | | MIN versus wild-type mice (%) | Patients with advanced adenomas versus neoplasia-free controls (%) |
| | 2 weeks after AOM treatment | 6 weeks after AOM treatment | | |
| Sensitivity | 84 | 100 | 88 | 100 |
| Specificity | 72 | 100 | 76 | 64 |

*Figure 16*

| Rectal marker | Two factor ANOVA p-value for the effect of age | Correlation coefficient |
|---|---|---|
| LEBS spectral slope | 0.59 | 0.02 |
| Correlation decay rate | 0.39 | -0.13 |
| LEBS enhancement | 0.51 | -0.05 |
| LEBS width | 0.73 | -0.01 |
| PCI | 0.52 | -0.03 |

*Figure 17*

SYSTEMS, METHODS, AND APPARATUSES OF LOW-COHERENCE ENHANCED BACKSCATTERING SPECTROSCOPY

CLAIM OF PRIORITY

This application claims priority to U.S. Patent Application No. 60/799,970 entitled "Low-Coherence Enhanced Backscattering Spectroscopy and Applications of Same", which was filed on May 12, 2006, the contents of which are expressly incorporated by reference herein.

CROSS-REFERENCE TO RELATED PATENT APPLICATION

This application is related to a copending U.S. patent application Ser. No. 11/261,452, entitled "MULTI-DIMENSIONAL ELASTIC LIGHT SCATTERING", filed 27 Oct. 2005 with the same assignee as the present disclosure. The applicants of that application are also applicants of this application. The disclosure of the above identified copending application is incorporated in its entirety herein by reference.

This application is related to a copending U.S. patent application Ser. No. 11/604,653, entitled "METHOD OF RECOGNIZING ABNORMAL TISSUE USING THE DETECTION OF EARLY INCREASE IN MICROVASCULAR BLOOD CONTENT", filed 27 Nov. 2005 with the same assignee as the present disclosure claiming priority to U.S. Application No. 60/801,947 entitled "GUIDE-TO-COLONOSCOPY BY OPTICAL DETECTION OF COLONIC MICRO-CIRCULATION AND APPLICATIONS OF THE SAME", filed 19 May 2006. The applicants of the above applications are also applicants of this application. The disclosure of the above identified copending applications is incorporated in its entirety herein by reference.

This application is further related to a copending U.S. patent application Ser. No. 11/604,659, entitled "APPARATUS FOR RECOGNIZING ABNORMAL TISSUE USING THE DETECTION OF EARLY INCREASE IN MICROVASCULAR BLOOD CONTENT", filed 27 Nov. 2005 with the same assignee as the present disclosure claiming priority to U.S. Application No. 60/801,947 entitled "GUIDE-TO-COLONOSCOPY BY OPTICAL DETECTION OF COLONIC MICRO-CIRCULATION AND APPLICATIONS OF THE SAME", filed 19 May 2006. The applicants of the above applications are also applicants of this application. The disclosure of the above identified copending applications is incorporated in its entirety herein by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, a superscript "["]" represents the nth reference cited in the reference list. For example, [24] represents the 24th reference cited in the reference list, namely, Backman, V. et al. Detection of preinvasive cancer cells. *Nature* 406, 35-36 (2000).

FEDERALLY-SPONSORED RESEARCH

This disclosure was made with Government support under Grant No. R01CA112315 and U01 CA111257 awarded by the National Institutes of Health of the United States, and under Grant No. BES-0238903 awarded by the National Science Foundation. Accordingly, the United States Government may have certain rights in this disclosure pursuant to these grants.

TECHNICAL FIELD

The present disclosure relates generally to light scattering, and in particular to low-coherence enhanced backscattering spectroscopy and/or applications of light scattering including medical diagnostic and treatment purposes.

BACKGROUND

Colorectal cancer remains one of the leading cause of cancer mortality in the United States. In 2006, there were approximately 55,170 estimated colorectal cancer (CRC) related deaths. Given early detection, early-stage colorectal cancer can be curable. However, given the insidious nature of colonic neoplasia, most patients are diagnosed when the cancer has evolved to a more advanced stage thus underscoring the need for effective screening of the at-risk population (e.g., those over 50 years of age) for early detection.

For example, existing colorectal cancer screening methods include fecal blood tests (FOBTs), endoscopy for direct visualization of the colon (e.g., flexible sigmoidoscopy or colonoscopy), and/or air-contrast barium enema. Although, the existing methods have been shown to demonstrate some efficacy in reducing colorectal cancer mortality and incidence, a large portion of the population does not undergo any endoscopic screening potentially due to patient and/or physician reluctance.

However, due to resource constraints and potential complications, it is impractical to perform colonoscopy on an entire at-risk population (e.g., those over the age of 50). In addition, for the general population the lifetime risk of developing CRC is approximately 6%. Thus performing colonoscopy on a large population to reach a relatively small sub-group of at risk population who may develop colonic neoplasia is cost and time inefficient.

Numerous techniques have been introduced for screening of colorectal cancer but have yet to demonstrate the robustness necessary for population screening. For example, reports of demonstrated performance of fecal DNA analysis were not statistically significant in multicenter trials. Further, the marked cost of fecal DNA analysis may be a barrier to wide spread usage.

From a radiological perspective, in single center studies, computed tomography colography (virtual colonoscopy) showed promise, unfortunately, the sensitivity demonstrated in multicenter trials have been unreliable. Furthermore, given the need for bowel cleansing and colonic air insufflation, there is no clear advantage in patient preference between CT colonography and colonoscopy. Given the high cost of CT colonography, it may be difficult to provide high quality CRC screening in a resource-constrained society.

Thus, there is a need to identify those more likely to harbor colonic neoplasia to target colonoscopy to these individuals. Such efforts can provide colonoscopy to a better defined set of patients more likely to be harboring neoplasia thereby sparing those patients who are unlikely to benefit from the cost, inconvenience, and potential complication of colonoscopy.

Pancreatic cancer is another leading cause of cancer death in the United States with most cancers diagnosed at a late, incurable stage. Existing approaches, including high-resolution imaging (MRI, CT, etc.), molecular diagnostics, and/or endoscopic cholangiopancreatography (ERCP), have not demonstrated the robustness in capability to detect pancreatic neoplasms sufficiently early to allow effective treatment.

Current imaging modalities as well as ERCP utilize detection of the presence of a mass lesion, and, therefore, even if the resolution of these tests is improved, the tumor detected may likely be biologically too advanced for cure. Despite years of research no clinically adequate molecular markers have been developed. The only route that currently has the potential for diagnosing pre-invasive cancer is through the pancreatic duct, where 90% of adenocarcinomas of the pancreas originate. Due to the potential for complications including pancreatitis (3-5% cases), as currently performed, ERCP may not be suitable for routine screening over successive points in time.

SUMMARY OF THE DESCRIPTION

Systems, methods, and apparatuses of low-coherence enhanced backscattering spectroscopy are described here. Some embodiments of the present disclosure are summarized in this section.

In one aspect, embodiments of the present disclosure include providing incident light comprising at least one spectral component having low coherence, wherein the incident light is to be illuminated on a target object in vivo, recording an intensity of one or more of at least one spectral component and at least one angular component of backscattering angle of backscattered light, wherein the backscattered light is to be backscattered from illumination of the incident light on the target object and wherein the backscattering angle is an angle between incident light propagation direction and of backscattered light propagation direction, and analyzing the intensity of the at least one spectral component and the at least one backscattering angle of backscattered light to obtain one or more optical markers of the backscattered light, toward evaluating said properties.

In another aspect, embodiments of the present disclosure include a light source to provide incident light having at least one spectral component, a plurality of optical components, wherein one or more of the plurality of optical components are operatively configured to determine a spatial coherence length of the incident light, and a receiving end to record an intensity of one or more of at least one spectral component and at least one angular component of backscattering angle of backscattered light, wherein the backscattered light is to be backscattered from illumination of the incident light on the target object and wherein the backscattering angle is an angle between incident light propagation direction and backscattered light propagation direction.

In yet another aspect, embodiments of the present disclosure include an apparatus couple-able to a light source and a target object, to facilitate light transmission between the light source to the target object, the apparatus comprising: a probe to emit incident light that is partially coherent light obtained from the light source onto the target object and to receive interacted light, the interacted light to be backscattered light from illumination of the incident light on the target object, the probe comprising: a delivery channel having at least one delivery optical fiber with a distal end portion couple-able to the light source and a proximal end portion suited to deliver the incident light to be projected on the target object, a collection channel having at least one collection optical fiber suited to collect light, the at least one optical fiber having a proximal end portion to receive the light to be backscattered from illumination of the partially coherent light on the target object, and a distal end portion adapted to be coupled to a receiving end, and a plurality of optical components optically coupled to the proximal end portion of one or more of the at least one delivery optical fiber and the at least one collection optical fiber, wherein one or more of the plurality of optical components are operatively configurable to select a spatial coherence length of the incident light.

In another aspect, embodiments of the present disclosure include providing incident light comprising at least one spectral component having low coherence, wherein the incident light is to be illuminated on a target object, recording an intensity of at least one spectral component and at least one angular component of backscattering angle of backscattered light, wherein the backscattered light is to be backscattered from illumination of the incident light on the target object and wherein the backscattering angle is an angle between incident light propagation direction and backscattered light propagation direction, recording an intensity of at least one spectral component and at least one angular component of backscattering angle of backscattered light, wherein the backscattered light is to be backscattered from illumination of the incident light on the target object and wherein the backscattering angle is an angle between incident light propagation direction and backscattered light propagation direction, and analyzing the intensity of the at least one spectral component and the at least one backscattering angle of backscattered light to obtain one or more optical markers of the backscattered light, toward evaluating said properties.

The present disclosure includes methods and apparatuses which perform these methods, including processing systems which perform these methods, and computer readable media which when executed on processing systems cause the systems to perform these methods.

Other features of the present disclosure will be apparent from the accompanying drawings and from the detailed description which follows.

BRIEF DESCRIPTION OF THE DRAWINGS

The disclosure is illustrated by way of example and not limitation in the figures of the accompanying drawings in which like references indicate similar elements.

FIG. 1A illustrates graphically the physical phenomenon of the constructive interference of time-reversed photons scattering in a material that results in enhanced backscattering, according to one embodiment.

FIG. 1B illustrates the angular distribution of the backscattering intensity of low-coherence enhanced backscattering spectroscopy (LEBS), according to one embodiment.

FIG. 3A illustrates a plot of the penetration depth of the incident light of LEBS as a function of the backscattering angle of the incident light, according to one embodiment.

FIG. 3B illustrates a plot of the penetration depth of the incident light of LEBS as a function of radial distance, according to one embodiment.

FIG. 14B is a set of bar diagrams illustrating the decay length obtained from the intensity of the LEBS backscattered light from the endoscopically and histologically normal mucosa of the rectum, according to one embodiment.

FIG. 14C is a bar diagram illustrating the full-width at half-maximum (FWHM) of an angular width of LEBS intensity plot obtained from the endoscopically and histologically normal mucosa of the rectum, according to one embodiment.

FIG. 16 is a table of calculated sensitivity and specificity of LEBS markers for predicting neoplastic risk, derived from the rat, mice, and human data, according to one embodiment.

FIG. 17 is a table showing results of correlation analysis between a patient's age and an LEBS marker, according to one embodiment.

DETAILED DESCRIPTION

Figure 2A:
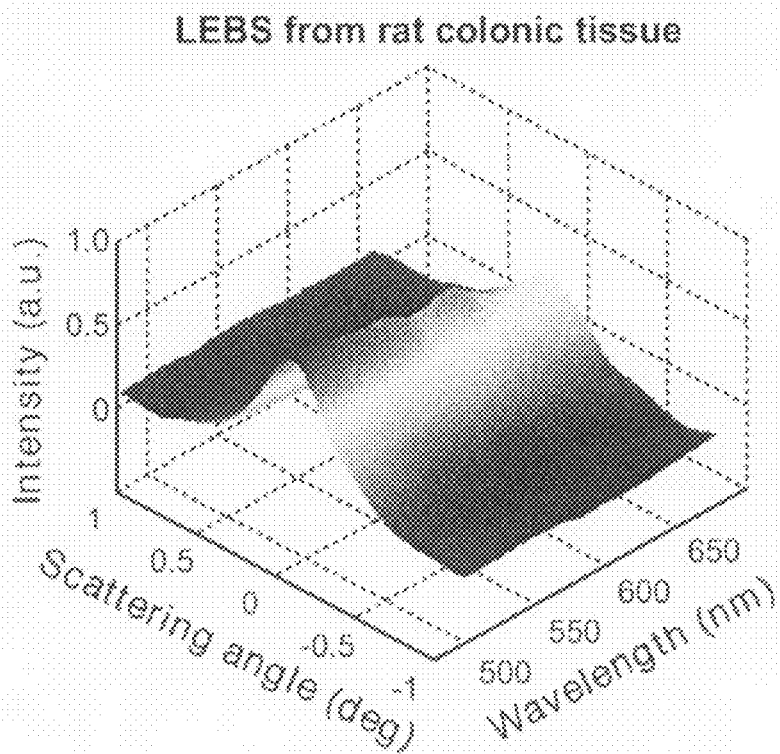
FIG. 2A illustrates a plot of LEBS backscattering intensity recorded from a rat colon tissue as a function of wavelength and scattering angle, according to one embodiment.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Without intent to limit the scope of the disclosure, exemplary instruments, apparatus, methods and their related results according to the embodiments of the present disclosure are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the disclosure so long as the disclosure is practiced according to the disclosure without regard for any particular theory or scheme of action Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Embodiments of the present disclosure include systems, methods, and apparatuses of low-coherence enhanced backscattering spectroscopy. In one aspect, the present disclosure relates to optically examining a target object for early detection of pre-neoplastic changes based on the field effect, or the concept that genetic/environmental milieu that results in a neoplastic lesion in one area of an anatomical region (e.g., the colon) should be detectable in uninvolved (e.g., colonoscopically normal-appearing) mucosa throughout the anatomical region (e.g., colon).

In one aspect, a probe comprises a light source configured and positioned to project a beam of light on a target object, a means to measure at least one spectral component of light scattered from the target object, and at least one angular component of light scattered from the target object. The probe apparatus may further include a detector to obtain the spectral data of the backscattered light. The spectral data can then be analyzed to determine if the target object having the tissue to be inspected is normal.

The neoplastic disease is at least part of a process leading to a tumor or lesion, where the tumor or lesion can be an abnormal living tissue (e.g., premalignant or cancerous), such as pancreatic cancer, a colon cancer, an adenomatous polyp of the colon, a liver cancer, a lung cancer, a breast cancer, and/or other cancers.

While abnormal tissue can be a lesion or tumor, the abnormal tissue can also be tissue that precede the development of dysplastic lesions that themselves do not yet exhibit dysplastic phenotype, and tissues in the vicinity of these lesions or pre-dysplastic tissues.

A particular application described herein is for detection of such pre-neoplastic changes in the colon in early colorectal cancer detection, other applications are described as well. Other biologically related application include monitoring of bioengineered tissue development. Yet other applications are contemplated beyond use of the invention in association with healthcare, such as characterization of polymer mechanical and molecular weight data, morphological structures of solid polymeric materials.

Coherent Backscattering (CBS)/Enhanced Backscattering (EBS)

Coherent backscattering (e.g., enhanced backscattering, CBS, or EBS) of light, originates from the constructive interference in elastic light scattering that gives rise to an enhanced scattered intensity in the backward direction. For a plane wave illuminating a semi-infinite random medium, photons scattered from the medium in the backward direction has a time-reversed photon traveling along the same path in the opposite direction (e.g., the path formed by exactly opposite sequences of the scattering centers). These photons have the same phase and thus interfere constructively with each other, resulting in an enhanced backscattering peak.

FIG. 1A illustrates graphically the physical phenomenon of the constructive interference of time-reversed photons scattering in a material that results in enhanced backscattering, according to one embodiment.

The phase difference between these two waves following the identical path in time reversed order is as shown. If phase difference is sufficiently small, constructive interference can occur. For backscattered light, the phase difference becomes very small, and thus, the two waves following the time-reversed paths interfere with each other constructively.

As shown in the figure, EBS originates from constructive interference between multiple photons propagating along a scattering light path (solid arrows) and the time-reversed path (e.g., dashed arrows) in the case when the photons exit the medium in directions close to the backscattering ($\theta \to 0$ deg). Thus, both waves have an identical phase when emerging from the medium thus constructively interfering with each other resulting in an enhanced scattered intensity in the backward direction, as shown on the intensity vs. backscattering angle plot of FIG. 1B.

Constructive interference occurs in the backscattering direction, whereas in directions sufficiently away from the backward direction, the constructive interference vanishes. In some situations, the peak EBS intensity can be twice as high as the incoherent intensity scattered outside the EBS peak (or background intensity).

The enhanced backscattering phenomenon can be investigated in a variety of different systems such as strong scattering materials, laser-cooled atoms, liquid crystals, photonic crystals, amplifying materials, and/or solar system bodies. Although the EBS phenomenon has attracted significant attention and can be observed in variety of nonbiological media, there has been few reports on EBS in biological tissue.

The lack of applications to biological samples may be due to the characteristics of EBS including: 1) conventional EBS peaks in tissue are narrow with angular width $w \approx \lambda/(3\pi I_s^*)$ ~0.001°, where $\lambda$ is the wavelength of light and $I_s^*$ is transport mean free path (in tissue $I_s^* \sim 500\text{-}2000$ μm); 2) experimental observation of such narrow peaks can be difficult; 3) EBS can be masked by speckle; 4) EBS measurements have not been shown to provide spectroscopic information, which is crucial for tissue diagnosis; and 5) conventional EBS does not enable depth-resolution. However, since most tissues have multi-layered structures, depth-resolution can be crucial for tissue diagnosis.

The enhanced backscattering peak profile can be further characterized by the distribution of path lengths of backscattered photons. For example, the dependency of the profile of the enhanced backscattering peak on the distribution of the path length can be studied using femtosecond-resolved measurements. Because the angular width of an EBS peak is proportional to the ratio of wavelength of light to the transport mean free path of light in the medium in biological tissue, the width of the EBS peak in tissue is narrow, typically w~0.001 degrees (w is the angular full width at half maximum of an EBS peak).

Quantitatively, the angular profile of an EBS peak $I_{EBS}(\theta)$ can be expressed as a 2-D Fourier transform of the radial intensity distribution of EBS:

$$I_{EBS}(\theta) \propto \int_0^\infty rP(r)\exp(i2\pi\theta/\lambda)dr$$

Thus, $I_{EBS}(\theta)$ is the Fourier transform of radial intensity probability distribution $rP(r)$ of the backscattered photons. As a result, in an EBS peak, longer light paths correspond to small scattering angles, while shorter light paths correspond to larger scattering angles.

Low-Coherence Enhanced Backscattering (LEBS)

In principle, in EBS, the conjugated time-reversed waves can interfere with each other when they are spatially coherent, that is, the first and last points on the scattering path are within the coherence area. Some EBS measurements have been conducted using coherent laser light sources with spatial coherence length $L_{SC} \gg l_s^*$. Under such spatially coherent illumination, conjugate time-reversed waves emerging from the surface of the sample can be capable of interfering with each other.

However, if light incident on a sample has a finite spatial coherence length, the conjugated time-reversed waves can interfere constructively with each other when they are spatially coherent. Thus, the angular profile of an EBS intensity $I_{EBS}(\theta)$ can be expressed as:

$$I_{EBS}(\theta) \propto \int_0^\infty C(r)rP(r)\exp(i2\pi\theta/\lambda)dr$$

A finite spatial coherence area acts as a spatial window rejecting long paths by preventing long traveling waves from interfering with each other. In other words, spatial coherence length limits r contributing to the EBS signal. Incoherent waves have no correlation in phase and generate the incoherent background intensity. Thus, if $L_{SC}$ is sufficiently short (e.g., $L_{SC} \ll l_s^*$), the low spatial coherence illumination can enable low-order scattering to contribute to the EBS peak, resulting in significant (e.g., several orders of magnitude) broadening of an EBS peak.

Characteristics of Low-Coherence Enhanced Backscattering Spectroscopy (LEBS)

Spectroscopic Measurements

Using LEBS spectroscopy, intensity profiles can be observed as a function of wavelength. Simultaneous measurement of the spectral and scattering angle distributions of backscattered light can enable simultaneous recording of the spectral (e.g., 400-700 nm) and scattering-angle (e.g., −7° to 7° from the backscattering direction) distributions of scattered light.

FIG. 2A illustrates a plot of LEBS backscattering intensity recorded from a rat colon tissue as a function of wavelength and scattering angle, according to one embodiment.

Several optical spectroscopic techniques have been demonstrated to be useful for tissue diagnosis and characterization including reflectance, light scattering, fluorescence, and other types of spectroscopy. Consequently, the analysis of LEBS spectra may be used to provide additional information about tissue architecture, its tissue characterization and diagnosis.

Speckle Reduction

Figure 2B:
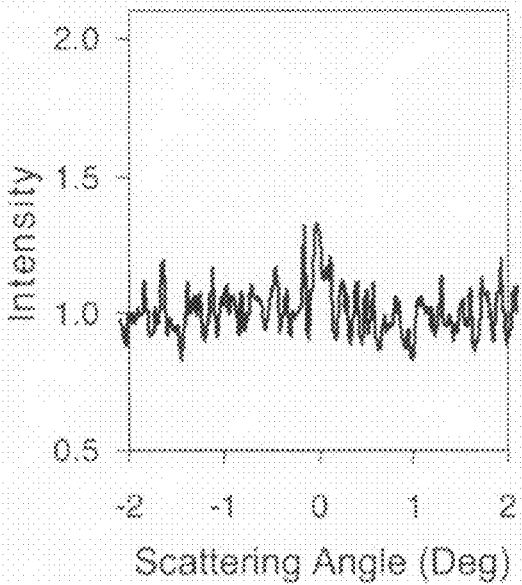
FIG. 2B illustrates a plot of the backscattering intensity as a function of the scattering angle in conventional EBS, according to one embodiment.

Experimental observation of LEBS may include ensemble or configuration averaging because of speckle, which arises from random interference effects. For example, rotating the sample mechanically or averaging independent measurements are used in conventional EBS measurements. Speckle becomes more severe in the absence of Brownian motion, hampering EBS studies in biological tissue. However, LEBS overcomes this problem. For comparison, FIG. 2B illustrates a plot of the backscattering intensity as a function of the scattering angle in conventional EBS, according to one embodiment.

The angular distribution of the backscattered light obtained from the same tissue site when a coherent He-Ne laser was used is shown. As can be seen, in the case of coherent illumination, the speckle masks the profile of an EBS peak. It has been shown that both low spatial and temporal coherence can contribute to speckle reduction. For example, for $L_{SC}\sim150$ μm, the number of independent coherence volumes $(D/L_{SC})^2 \times (l/L_{SC})\sim1000$, where D is the diameter of illumination area on the sample and l is the average path length. Therefore, LEBS measurements can be easily achieved in random media, even in the absence of Brownian motion without the need for ensemble or configuration averaging.

Figure 2C:
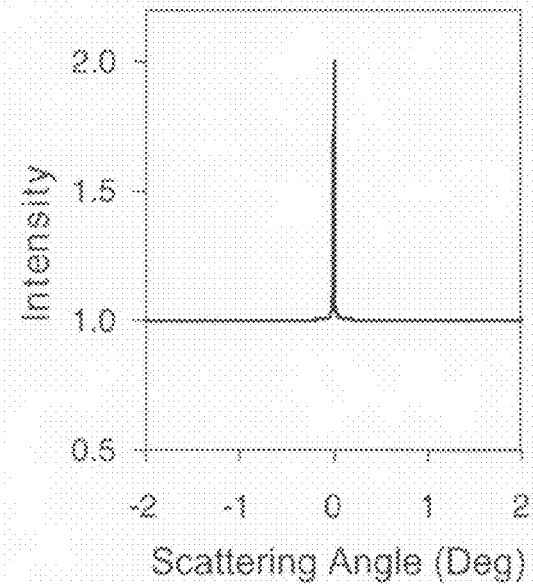
FIG. 2C illustrates a plot of the backscattering intensity as a function of the scattering angle in LEBS which is speckle-free, according to one embodiment.

FIG. 2C illustrates a plot of the backscattering intensity as a function of the scattering angle in LEBS which is speckle-free, according to one embodiment.

As can be seen, in the case of the LEBS signal recorded from the same tissue site, speckle is negligible and an enhanced backscattering peak can be identified. Both low spatial coherence illumination and low temporal coherence detection contribute to speckle reduction.

Broadening of Enhanced Backscattering Peaks

Broadening of EBS under low coherence illumination facilitates experimental observation of LEBS. Since the width of a conventional EBS peak in general is inversely proportional to $l_s^*$, the width of an EBS peak in tissue and other random media with long $l_s^*$ is narrow, typically w ~0.001 deg. On the other hand, an LEBS peak is broader with w~0.5 deg, which is approximately more than 100 times greater than the width of a conventional EBS peak expected under spatially coherent illumination. The width of LEBS is increased because it is predominantly generated by photons traveling short paths, restricted by a short spatial coherence length.

Depth-selective low-coherence enhanced backscattering measurements

Low spatial coherence illumination rejects long traveling paths and enables low-order scattering to contribute to the EBS thus allowing selectively probing superficial tissue. Because the superficial tissue layer (i.e., the epithelium) which can be as thin as 20-40 μm, is typically the first affected in carcinogenesis. For example, selective probing of CRC-significant cells, such as the colon stem cells in the base of the crypt can be achieved via LEBS examination.

In addition, hemoglobin (Hb) absorption in the blood vessels located underneath epithelium, but not within epithelium can obscure the endogenous spectral signatures of epithelial cells. This difficulty can be resolved using depth selectivity of LEBS.

Depth-selective LEBS spectroscopy of tissue can be achieved by three means: 1. Varying coherence length $L_{SC}$, 2. Analysis of LEBS spectra $I_{EBS}(\theta)$ at different scattering angles, and 3. Analysis of the radial intensity probability distribution of LEBS photons P(r), which can be obtained via the Fourier transform of $I_{EBS}(\theta)$. In brief, $L_{SC}$ determines the maximum penetration depth. Then, detailed depth-resolution can be obtained by either means 2 or 3.

Control of Tissue Depth Probed with LEBS Via Coherence Length

Photons emerging from the tissue surface at distances $r < \sim L_{sc}$ from the point of entry into the tissue can more effectively contribute to LEBS. Thus, the depth of penetration of LEBS photons is approximately $\sim L_{sc}$.

Control of Tissue Depth Probed with LEBS Via the Analysis of $I_{EBS}(\theta)$ at Different $\theta$ FIG. 3A illustrates a plot of the penetration depth of the incident light as a function of the backscattering angle of the incident light, according to one embodiment.

Because $I_{EBS}(\theta)$ is the Fourier transform of P(r), short light paths (e.g., small r) mainly give rise to the periphery of an LEBS peak (e.g., large $\theta$), while longer light paths (r~$L_{SC}$) give rise to the top (or center) of the LEBS peak ($\theta \rightarrow 0$ deg). This property of LEBS can be used to sample various depths using a single LEBS measurement by analyzing $I_{EBS}(\theta)$ at different $\theta$.

Small $\theta$ corresponds to deeper penetration depths, whereas large $\theta$ corresponds to shorter depths. Therefore, different depths can be selectively assessed by probing a corresponding scattering angle. For example, in the case of colonic mucosa, $I_{EBS}(\theta=0.25$ deg) enables assessment of an epithelial cell layer (~40 μm), whereas $I_{EBS}(\theta=0$ deg) allows probing the entire mucosa (~70 μm).

Control of Tissue Depth Probed with LEBS Via the Analysis of P(r) at Different r FIG. 3B illustrates a plot of the penetration depth of the incident light of LEBS as a function of radial distance, according to one embodiment.

For example, as shown in FIG. 3B, tissue depths from ~40 μm (e.g., a single cell layer) to ~100 μm (e.g., thickness of colonic mucosa) can be selectively assessed by means of the analysis of P(r, λ) by choosing appropriate parameter r. Thus, LEBS spectroscopy enables the possibility of performing spectroscopic measurements at any given depth within the maximum penetration depth determined by $L_{SC}$.

Figure 4A:
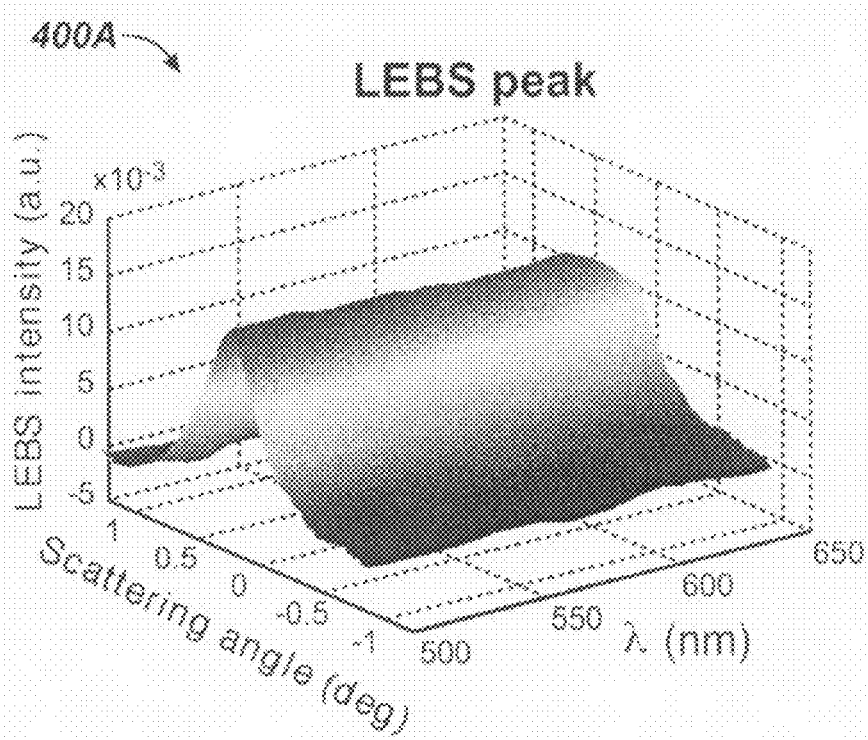
FIG. 4A illustrates a plot of an LEBS intensity plot as a function of the backscattering angle, according to one embodiment.

FIG. 4A illustrates a plot of an LEBS intensity plot as a function of the backscattering angle, according to one embodiment.

Figure 4B:
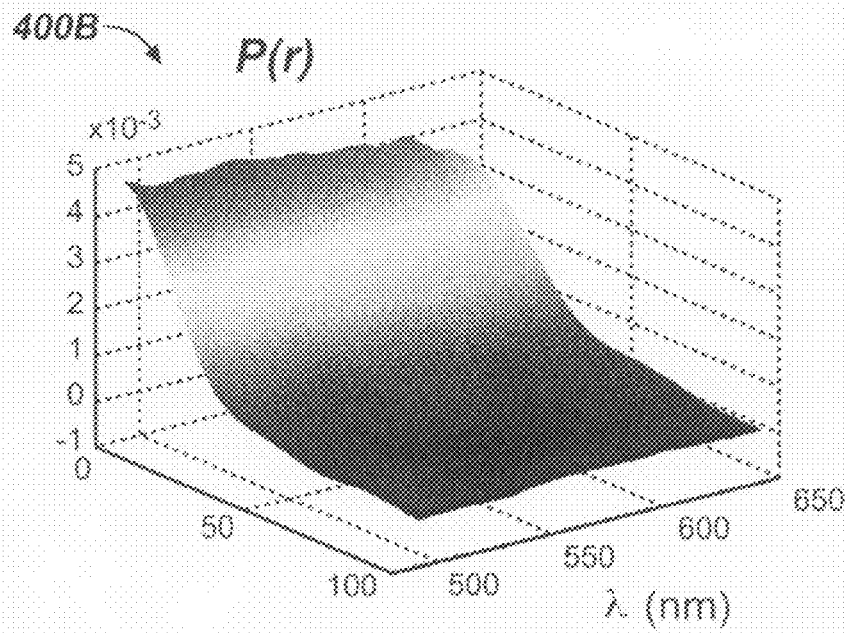
FIG. 4B illustrates a plot of the angular distribution of the Fourier transform of the LEBS intensity plot, according to one embodiment.

FIG. 4B illustrates a plot of the angular distribution of the Fourier transform of the LEBS intensity plot, according to one embodiment.

A more precise control of tissue depth probed with LEBS can be achieved by means of the analysis of P(r), which can be obtained from the Fourier transform of $I_{EBS}(\theta)$. Thus, the depth of penetration of photons increases with r.

To investigate depth selectivity with LEBS, a two layer tissue phantom was prepared as solid phantom and comprises agarose gel-imbedded suspension of red blood cells to mimic light absorption in tissue and 0.43 μm polystyrene microspheres to mimic tissue scattering.

Figure 5A:
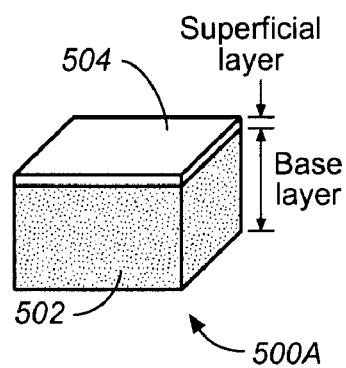
FIG. 5A is schematic illustrating a two-layer tissue sample comprising a superficial layer and a base layer, according to one embodiment.

FIG. 5A is schematic illustrating a two-layer tissue sample 500A comprising a superficial layer 504 and a base layer 502, according to one embodiment.

In one embodiment, the thickness of the base layer 502 was approximately $T_B$=6 mm and the superficial layer 504 does not contain any red blood cells, thus analogous to avascular epithelium situated on top of a thick stroma. The physical thickness of the superficial layer $T_S$ 504 can vary from 0 to 35 μm. In one embodiment, the LEBS intensity spectra, $I_{LEBS}(\theta)$ for various values of the thickness of the superficial layer $I_{LEBS}(\theta)$ is integrated over scattering angle within the LEBS peak at any given wavelength.

If a LEBS signal is contributed by photons propagating in both superficial and base layers (i.e., a photon path is sufficiently long so that it extends to the base layer), the LEBS spectrum should exhibit characteristic hemoglobin (Hb)-absorption bands at around 550 nm. If the superficial layer is sufficiently thick such that the LEBS signal is primarily contributed by photons with paths within the superficial layer, the LEBS spectrum may not exhibit Hb-absorption.

Figure 5B:
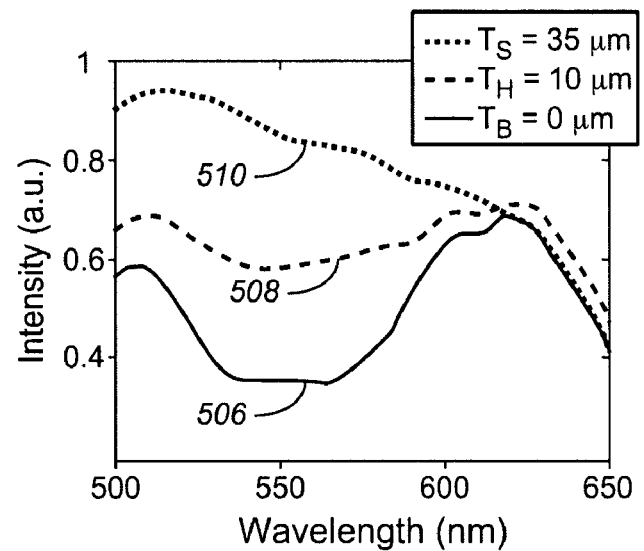
FIG. 5B is a plot illustrating the LEBS intensity spectra recorded from the two layer tissue sample for various values of thickness of the superficial layer, according to one embodiment.

FIG. 5B is a plot illustrating the LEBS intensity spectra recorded from the two layer tissue sample for various values of thickness of the superficial layer, according to one embodiment.

As shown, the LEBS intensity recorded from the base-layer alone 506 ($T_S$=0 μm) shows the characteristic Hb-absorption bands at approximately 550 nm. However, as the thickness of the superficial layer is increased, the Hb-absorption band gradually vanishes. For the intensity recorded from $T_S$=10 μm 508, the influence of Hb-absorption is significantly reduced, thus indicating that a major contribution to the LEBS originates from the superficial 10-μm-thick layer.

When the thickness of the superficial layer is increased farther to $T_S$=35 μm in dataset 510, the LEBS spectrum does not exhibit observable Hb-absorption bands, thus indicating that the LEBS signal is contributed by photons which travel within the superficial layer. This result provides evidence that the low-coherence LEBS is contributed by very short path lengths, which are in the order of $L_c$.

The significance of depth-selective spectroscopic measurements for tissue characterization and diagnosis is underscored by the following reasons.

1. The most superficial tissue layer (i.e., the epithelium) is the origin of nearly 90% of human cancers and the epithelial cells are the first affected in carcinogenesis. Thus, obtaining diagnostic information from most superficial tissue is crucial for the early diagnosis of epithelial precancerous lesions.
2. Hemoglobin absorption in the blood vessels located underneath the epithelium is a particularly notorious problem, as it obscures the endogenous spectral signatures of epithelial cells.
3. The depth-dependent biological heterogeneity of the epithelium underscores the need to selectively assess the epithelial cells at different depths. For example, in the colon (the major unit of organization of the mucosa is the crypt), the epithelial cells at the base of the crypt (~80 μm below the tissue surface) are capable of proliferation, while the epithelial cells at the top of the crypt (~40 μm) undergo apoptosis, as illustrated in FIG. 5C.

Figure 5C:
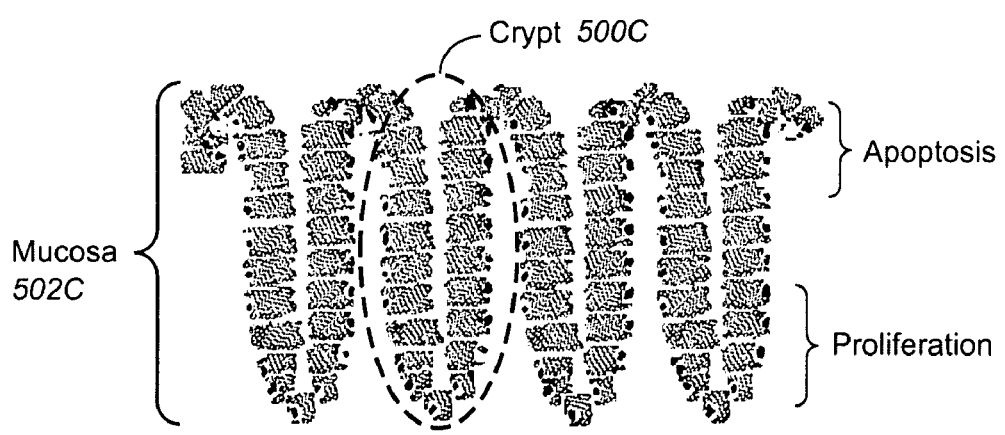
FIG. 5C is a plot illustrating the crypt: the major unit of the colonic mucosa, according to one embodiment.

FIG. 5C is a plot illustrating the crypt 500C: a major unit of the colonic mucosa 502C, according to one embodiment.

The epithelial cells have distinct cell activities at various depths. A typical depth of a colonic crypt can be 70-90 μm. In adenomatous colonic mucosa, the apoptotic activity can be reduced in the base of the crypt while the proliferative activity is increased in the lumenal surface of the colon. The cells that are initially involved in neoplastic transformations are located in a specific area of the crypt: the base of the crypt is known as the location for initiation of colon carcinogenesis. Similar considerations apply to most other types of epithelia, including stratified squamous epithelium (e.g., the epithelium of uterine cervix, oral cavity, etc.).

Light scattering in biological tissue has been of great interest for tissue characterization and diagnosis. Results obtained by a number of investigators have proven that light scattering can provide diagnostically valuable information about tissue structure and composition, The most superficial tissue layer (i.e., the epithelium) is the origin of nearly 90% of human cancers and the epithelial cells are the first affected in carcinogenesis. Thus obtaining diagnostic information from most superficial tissue is crucial to the early diagnosis of epithelial precancerous lesions.

Differentiation between photons whose paths are limited to a superficial tissue layer and those traveling longer paths extending deep into the tissue requires specialized techniques, because the dominant portion of the light returned from the tissue is scattered multiple times from depths up to several Is*. Time-gating techniques use early-arriving photons to eliminate long-traveling photons. Polarization gating has been successfully used to distinguish between single and multiple scattering based on the depolarizing effect of multiple scattering.

The spectral analysis of the polarized component can be further used to obtain quantitative information about the morphology of superficial epithelial cells and to achieve imaging of superficial tissue.

LEBS enables the analysis of tissue organization at scales otherwise inaccessible to conventional microscopic or imaging techniques and ranging from a few tens of nanometers (below the resolution of optical microscopy used for histologic analysis of tissue structure) to microns. Thus LEBS has enabled gathering of unattainable quantitative information about nano/microscale tissue architecture in situ.

For example, it has been demonstrated in animals studies that LCBS spectroscopy is shown as a new technique for depth-selective tissue diagnosis and can be used to identify pre-neoplastic changes in the initial stages of carcinogenesis, far earlier than is currently possible using any histological, molecular, or genetic means. Thus, LEBS can be used to detect early precancerous lesions earlier than it is feasible using other available techniques. Furthermore, data demonstrating that LEBS may allow screening for colon cancer without colonoscopy has been established.

Field Effect

Some cancer risk stratification techniques exploit the "field effect," the concept that assessment of biomarkers in one area of the colon should be able to determine the likelihood of current/future neoplastic lesions throughout the colon. For example, the genetic/environmental milieu that results in a neoplastic lesion in one area of the colon can be detectable in uninvolved (i.e., colonoscopically normal-appearing) mucosa throughout the colon.

There exists evidence to support the molecular underpinnings of the microarchitectural changes noted in the histologically normal "field." For instance, Chen et al. recently reported that a panel of proto-oncogenes, including cyclooxygenase 2 and osteopontin, were markedly over expressed in histologically normal mucosa of patients harboring colorectal cancer. This is also noted in the preneoplastic MIN mouse and, importantly, the magnitude of proto-oncogenes overexpression was in-between control intestinal epithelium (C57BL/6 mice wild type at APC) and adenomatous/carcinomatous tissue, arguing for the relevance of these changes to tumorigenesis. Furthermore, work by Cui et al. have noted that another epigenetic event (e.g., loss of insulin growth factor II imprinting) was increased in the uninvolved mucosa of patients with who harbored adenomas.

A commonly used clinical example is the identification of the distal and proximal adenoma or carcinoma on flexible sigmoidoscopy to predict the occurrence of neoplasia in the proximal colon. Other attempts include correlation of rectal aberrant crypt foci (ACF) using chromoendoscopy with colonic adenoma or carcinomas and carcinomas. Unfortunately, the performance characteristics of the existing markers remain suboptimal (e.g., the sensitivity and positive predictive value for the ability of flexible sigmoidoscopy to detect advanced proximal lesions are 40% and 6%, respectively.

Thus, currently available morphologic markers for the field effect are inadequate for risk stratification. Several lines of evidence suggest that the field effect has the potential of being sensitive at identifying patients with colonic neoplasia. Studies have reported that in the histologically normal mucosa of subjects harboring colonic neoplasia, there are profound genetic and epigenetic alterations in the field effect. However, detecting these molecular events with a methodology that would be feasible in clinical practice has been challenging.

It has been demonstrated by LEBS technology to identify colon carcinogenesis risk throughout the colon through detection of the field effect. Data obtained from azoxymethane-treated rat model of colon carcinogenesis show alterations in LEBS markers at time points that precede ACF or adenoma or carcinoma formation. Furthermore, these markers progress over time consonant with the progression of carcinogenesis. These results were replicated in the genetic model of intestinal carcinogenesis (the MIN mouse).

In human studies, LEBS analysis of the endoscopically normal mucosa is observed to be able to detect differences in patients who harbored adenoma or carcinomas when compared with those who were neoplasia free. Biological sample comprising tissue undergoing neoplastic transformation can be obtained in situ or examined in vivo. Thus, the technical advance of LEBS may potentially translate into a practical means for colon cancer screening. As discussed, the exploitation of the field effect is a strategy in colorectal cancer screening (e.g., assessment of distal adenoma or carcinomas or ACF). To improve sensitivity, others have proposed looking at cellular (apoptosis and proliferation) and biochemical variables (e.g., protein kinase C); however, the performance characteristics currently lack suitability for clinical practice.

In one embodiment, the analysis of mucosal nanoarchitectural and microarchitectural markers by means of LEBS exceeded the classic morphologic and/or biochemical markers. For example, the risk of neoplasia was assessed in the visually normal colonic mucosa rather than to detect morphologic lesions polyps. The neoplastic transformation may lead to various types of cancer, such as pancreatic cancer, colon cancer, liver cancer, lung cancer, esophageal cancer, stomach cancer, cervical cancer, oral cavity cancer, ovarian cancer, breast cancer, bladder cancer, cholangiocarcinoma, prostate cancer, and/or head and neck cancer, which can be detected via LEBS screening.

Spectral Slope

Spectral behavior of $I_{EBS}(k)$ depends on the size distribution of light-scattering structures. Generally, $I_{EBS}(k)$ is a declining function of wavelength, and the steepness of the decline can be related to the relative portion of structures of different sizes. Larger structures that approach micron and supra-micron sizes (i.e., cellular organelles, etc.) tend to reduce the steepness of the change of $I_{EBS}(k)$ over wavelength, whereas smaller scatterers (sizes as small as ~20 nm) tend to increase the steepness of $I_{EBS}(k)$ over wavelength.

To characterize $I_{EBS}(k)$ with a single variable, linear fits to $I_{EBS}(k)$ can be obtained using linear regression from 530 to 640 nm. The absolute value of the linear coefficient of the fit is referred to as the "LEBS spectral slope" and quantifies the dependence of an LEBS spectrum on wavelength.

Spectral Exponential

Similarly $I_{EBS}(k)$ can vary based on the exponential power of the wavelength. For example $I_{EBS}(k) \propto \lambda^{-\alpha}$, where $\alpha$ is referred to as the spectral exponential.

Autocorrelation Decay Rate

Autocorrelation of LEBS spectra is, $C_A(\Delta k) = \int I_{EBS}(k) I_{EBS}(k+\Delta k) dk$, where k is the wave number. The autocorrelation of the LEBS spectra can reveal the degree of refractive index fluctuations in tissue micro-architecture of the optically examined sample. It is determined that, $C_A(\Delta k) \propto \exp(-\Delta k^2 D)$, characteristic of random mesoscopic systems where D is the decay rate. $D \propto (\delta n^2 L_C/L_t)^{-1} \lambda^2$, where $\delta n^2$ is the variance of refractive index fluctuations, $L_C$ is the refractive index correlation length, and $L_t$ is the temporal coherence length of illumination. It was determined that the decay rate D was decreased in patients with adenoma or carcinomas (p<0.016).

In addition, the autocorrelation decay rate of the backscattered light intensity as a function of backscattering angle $I_{LEBS}(\theta)$ can also be determined in a similar fashion such as that outlined above and can be utilized as an LEBS optical marker.

Peak Width and Enhancement Factor

The low coherence enhanced backscattering peak at the center of angular distribution (i.e., LEBS peak) can be determined in both angular and spectral dimensions. The angular profile of LEBS peak $I_{LEBS}(\theta)$ can be used to calculate the full-width at half maximum and enhancement factor of the LEBS intensity. The width and the enhancement factor have been demonstrated to be sensitive to optical properties of tissue architecture, such as scattering coefficient and optical density. The peak width of LEBS can be characterized as the full-width at half maximum (e.g., FWHM) of the LEBS peak $I_{LEBS}(\theta)$ averaged within a predetermined wavelength range (e.g., from 620 to 670 nm). The enhancement factor is defined as the ratio of the LEBS peak intensity $I_{LEBS}$ ($\theta=0°$) to the incoherent baseline intensity $I_{BASE}(\theta)$ outside of the LEBS peak, which can be measured for larger angles of backscattering (e.g., $\theta>3°$) for substantially similar wavelength ranges.

The spectral behavior of the LEBS signal primarily depends on the second-order scattering of weakly localized photons by tissue structures, which is a contrast mechanism that is not easily probed by other existing techniques. The spectrally resolved LEBS signals can be normalized as: $I_{EBS}(\theta,\lambda) = (I(\theta,\lambda) - I_{BASE}(\lambda))/I_{REF}(\lambda)$, where $I_{BASE}$ is the baseline (incoherent) intensity and $I_{REF}$ is the reference intensity collected from a reflectance standard (this normalization to account for the non-uniform spectrum of the incident light illumination and the spectral response of detection).

Fourier Transform of $I_{LEBS}(\theta)$

The Fourier transform of the angular profile of LEBS peak $I_{LEBS}(\theta)$ can be used to calculate the decay rate of the transform with respect to the independent Fourier variable. For example, the $$\text{decay rate is } \frac{d}{dr} P(r),$$

where $P(r) = FT\{I_{LEBS}(\theta)\}$.

The decay rate can be sensitive to optical properties of tissue architecture, such as scattering coefficient and optical density.

Principal Component Index

In addition, principal component analysis (PCA) of LEBS spectra can be performed. The first two principal components (PC1 and PC2) were determined to accounted for ~99% of the data variance. In search for an LEBS marker based on PCA, the PC index (PCI) was defined as a linear combination of PC1 and PC2 and PCI=PC1+5PC2 was determined to be the most significant. The PCI index was found to be significantly decreased at two weeks time point (p-value<0.02) and continued to progressively decrease over the course of the experiment (p-value<0.000001). The temporally progressive change in PCI indicates that it is not due to an acute side-effect of AOM.

In one embodiment, incident light comprising at least one spectral component having low coherence is provided. For example, the incident light is to be illuminated on a target object an intensity of at least one spectral component and at least one angular component of backscattering angle of backscattered light, wherein the backscattered light is to be backscattered from illumination of the incident light on the target object and wherein the backscattering angle is an angle between incident light propagation direction and backscattered light propagation direction. Further, the intensity of the at least one spectral component and the at least one backscattering angle of backscattered light can be analyzed to obtain one or more optical markers of the backscattered light.

In one embodiment, the spatial coherence length of the incident light can be adjusted to select a depth of penetration of the target object by the incident light. For example, the depth of penetration is substantially the spatial coherence length of the incident light. The depth of penetration of the incident light can be determined based on at least one angular component of the backscattering angle of the backscattered light.

The incident light can be projected onto the target object having an angle of incidence greater than zero degrees (e.g., ~15 degrees) to mitigate specular reflection from the target object, wherein the angle of incidence is the angle between the incident light propagation and a direction normal to the target object. In one embodiment, at least one spectral component of the backscattered light is collected to detect backscattered light having low temporal coherence length. The recording of the intensity includes recording a matrix of intensities of backscattered light as a function of wavelength and backscattering angle.

In one embodiment, the depth of penetration of the target object by the incident light is identified where the optical marker of the backscattered light is sensitive to biological changes of the target object. The optical marker can be obtained from tissue of an anatomical region proximal to tissue of the anatomical region potentially harboring adenoma or carcinoma. The presence of adenoma or carcinoma can be detected in at least a part of the colon via detecting optical changes via at least one optical marker from tissue obtained from anywhere in the colon.

Figure 6:
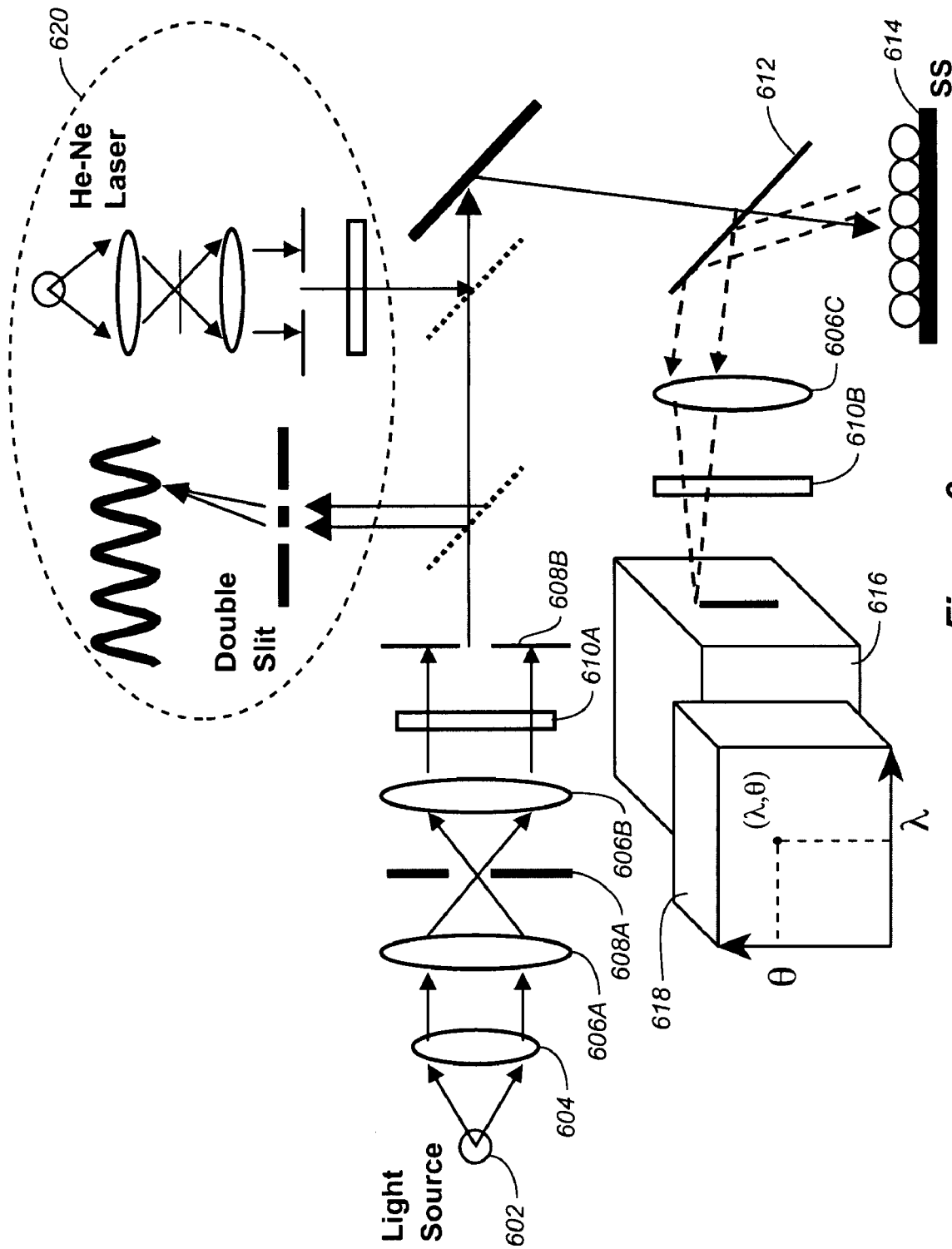
FIG. 6 is a schematic of an LEBS instrument having a plurality of optical components for LEBS spectroscopy, according to one embodiment.

FIG. 6 is a schematic of an LEBS instrument having a plurality of optical components for LEBS spectroscopy, according to one embodiment.

To achieve low-coherence enhanced backscattering (LEBS) spectroscopy, EBS can be combined with low spatial coherence and broadband illumination, and spectrally resolved detection. In one embodiment, a light source 602 (e.g., 500W xenon lamp) is to deliver incident light, or a beam of multi-band light (e.g., broadband light). The beam of multi-band light can be collimated by a plurality of optical components. For example, the beam of broadband light is collimated via a 4-f lens system including a lens-aperturelens combination (e.g., the lens 606A, the aperture 608A, and the lens 606B), and a condenser 604. In one embodiment, the beam of light is collimated via a lens and an aperture.

In one embodiment, the incoming beam is further polarized via a polarizer 610A and projected onto the sample stage 614. The angle of incidence of the incident light upon the sample stage can be greater than zero degrees to mitigate specular reflection from the target object. The angle of incidence is the angle between the incident light and a direction normal to the sample stage.

In one embodiment, the spatial coherence length of the illumination beam $L_{SC}$ can be varied (e.g., between 100-200 μm) by means of the aperture 608A positioned in the Fourier plane of the lens system 606A/B in the light delivering arm of the instrument.

In addition, the spatial coherence length can be confirmed by double-slit experiments. For example, the laser, double-slit arm, and lens shown in the dotted circle 620 can be provided for testing and calibration purposes during research. Therefore, the components shown in 620 are not necessary to utilize full functionality of the LEBS system and hence may or may not be included in an LEBS system or probe.

In one embodiment, the backscattered light by the target object on the sample stage is collected using a lens (e.g., a Fourier lens 606C), a polarizer 610B (e.g., oriented along the polarization of the incident light), and an imaging spectrograph 616 positioned substantially in a focal plane of the lens 606C and coupled with an imaging device (e.g., a CCD camera 618). The lens can project the backscattered light on the slit of the spectrograph based on the angular distribution of the light. Therefore, scattered rays with a substantially similar scattering angle can be focused on a point on the entrance slit of the spectrometer. The above mentioned lenses can be any of a Fourier lens, a ball lens, a graded refractive index lens, an aspheric lens, cylindrical lens, convex-convex lens, and plano-convex lens.

In one embodiment, the imaging spectrograph is to disperse the light according to the frequency components (e.g., spectral components) of the backscattered light in the direction substantially perpendicular to the slit. Thus, the imaging device (e.g., CCD, photodetector, etc.) can record a matrix of the intensity of backscattered light as a function of wavelength k and backscattering angle θ.

For example, in a CCD pixel, collected light can be integrated within a certain bandwidth (e.g., Δk around k), according to one embodiment. Because the temporal coherence of light $L_{ct}$ is related to the spectral composition of the light, finite-band spectral detection can result in low temporal coherence detection. Thus, the temporal coherence length $L_{ct}$ can be determined by adjusting the spectral resolution of the spectrograph. For example, $L_{ct} = \sqrt{2\ln2/\pi}(\lambda^2/\Delta\lambda) \approx 30$ μm when Δλ~9 nm, is the full-width at half maximum (FWHM) of the detection band-pass.

In one embodiment, the system is to illuminate light on a target object. The target object can be a sample related to a living subject. The sample can be a portion of the living subject. In one embodiment, the sample is a biological sample wherein the biological sample may have tissue developing a cancerous disease or undergoing neoplastic transformation. The cancerous disease may be a tumor that is one of a pancreatic cancer, colon cancer, liver cancer, lung cancer, and breast cancer.

In one embodiment, the system includes a light source to provide incident light having at least one spectral component, a plurality of optical components to collimate the incident light, and/or a receiving end to record an intensity of at least one spectral component and at least one angular component of backscattering angle of backscattered light, wherein the backscattered light is to be backscattered from propagation of the incident light on the target object and wherein the backscattering angle is an angle between incident light propagation direction and backscattered light propagation direction. The light source may obtain the at least one spectral components of light from a plurality of narrowband light sources.

In one embodiment, the plurality of optical components comprises a lens and an aperture. The lens may be a positive lens. The lens can also be at least one of a Fourier lens, a ball lens, a graded refractive index lens, an aspheric lens, cylindrical lens, convex-convex lens, and plano-convex lens.

In one embodiment, the plurality of optical components comprises a two lens 4-f system and an aperture. The aperture can be disposed substantially in a common focal plane of the two lenses. The receiving end may further include a spectrometer to disperse the backscattered light according to the spectral component of the backscattered light on a spectrogram.

In one embodiment, the plurality of optical components further includes a lens to project the angular distribution of the backscattered light on the spectrometer. The receiving end may further include a light detector. For example, the light detector is a CCD camera or a plurality of photodetectors. In one embodiment, the plurality of optical components are adjustable to vary a spatial coherence length of the incident light. The spatial coherence length of the incident light can be varied to select a depth of penetration of the target object by the incident light. In one embodiment, the spatial coherence length of the incident light is adjusted based on the spatial coherence length of a light source. For example, a light source having light with a longer spatial coherence length increases the spatial coherence length of the incident light.

In one embodiment, the spatial coherence length of the incident light based on an angle of divergence of the incident light. For example, an increased angle of divergence decrease the spatial coherence length of the incident light.

The optical measurements of a sample can be acquired ex vivo, as well as in vivo. Development of fiber optic LEBS probes can facilitate translation of LEBS into clinical practice since the fiber optic LEBS probes can be used to record LEBS spectra from rectal mucosa in vivo and assess LEBS markers without having to perform colonoscopy or to obtain a biopsy. The probe can receive partially coherent input light from the Xe-lamp of the LEBS instrument and deliver in onto tissue surface. The probe can also collect the backscattered light from the target object as a function of scattering angle θ and deliver it to the imaging spectrometer and an imaging device (e.g., a CCD).

Examples of Probe Configurations

Figure 7A:
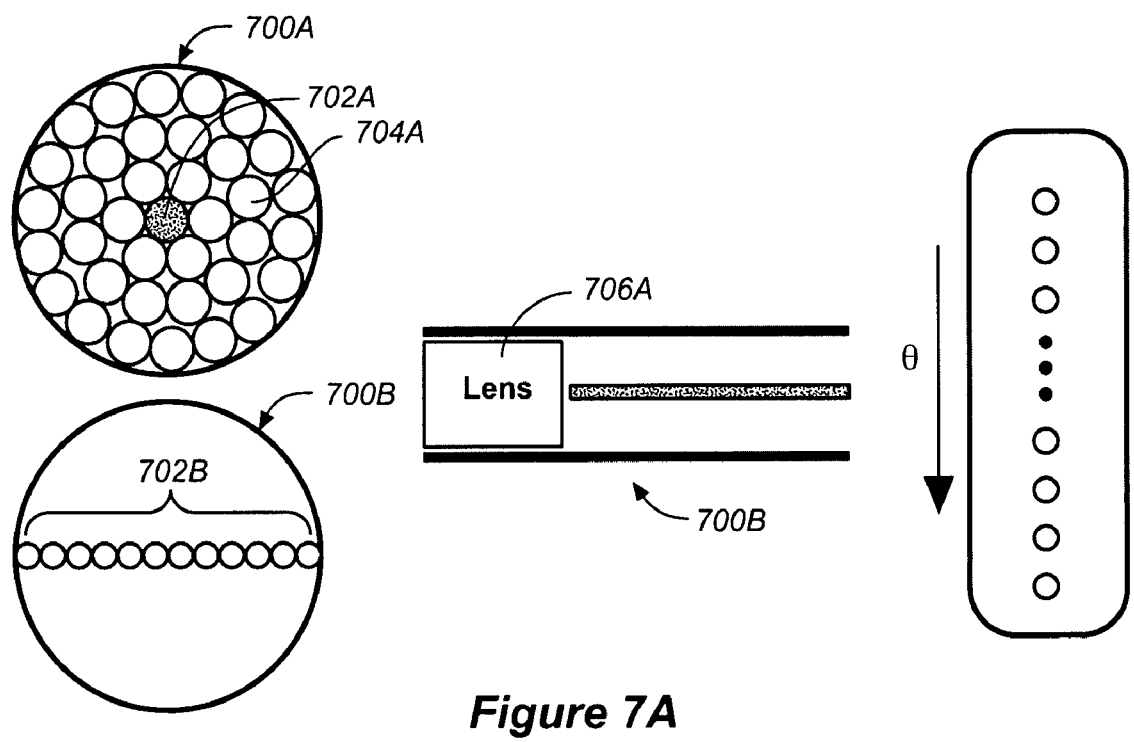
FIG. 7A is a set of cross sectional views of an endoscopic LEBS probe, according to one embodiment.

FIG. 7A is a set of cross sectional views of an endoscopic LEBS probe 700A, according to one embodiment (a): Illustration of a cross section of the probe tip. (b): Illustration of an output end of the probe. (c): Illustration of a longitudinal section of the probe.

In one embodiment, the probe includes at least one illumination fiber in the illumination channel 702A, and at least one collection fiber of the collection channel 704A. The illumination channel 702A can be positioned near the edge of the probe 700A or in the center of the probe 700A. In one embodiment, the illumination channel 702A is surrounded by the collection channel 704A. Furthermore, a set of a microprisms and a mirror can be used to separate the incident beams and the backscattered light.

In one embodiment, a lens 706A is positioned approximately one focal length from tip of the optical fibers. Analogously to the Fourier lens in the LEBS instrument of FIG. 6, the lens 706A can focus the backscattered light on different fibers based on the backscattering angle θ of the backscattered light. At the output end of the probe, the fibers can be arranged in the probe with a position based on the respective backscattering angle θ. In one embodiment, the array of fibers can be coupled to the light-collection arm (e.g., receiving end) having a number of analysis components (e.g., a polarization analyzer, imaging spectrograph, and/or an imaging device (CDD)). The above mentioned lenses can be any of a Fourier lens, a ball lens, a graded refractive index lens, an aspheric lens, cylindrical lens, convex-convex lens, and piano-convex lens. Lenses other then the above mentioned lenses can also be used.

The imaging device (e.g., the CDD) can record a matrix with an axis corresponding to the wavelength of light and the other axis with the angle of scattering (e.g., backscattering angle θ). Thus, in one embodiment, the probe can be fitted into an accessory channel of a colonoscope (e.g., outer diameter <2 mm), endoscope, or laparoscope. In one embodiment, the illumination stop size (~1 mm) is ideal to sample a sufficient number of epithelial cells and speckle spots (e.g., >200 independent speckle spots) for speckle reduction. In one embodiment, specular reflection form tissue-air and other interfaces does not affect the collected signal.

Figure 7B:
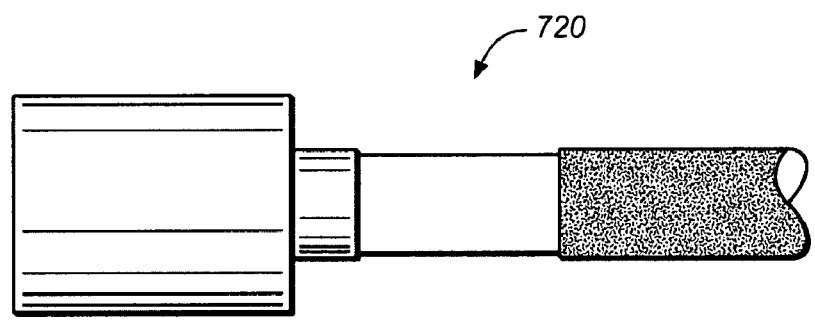
FIG. 7B is a graphical representation of an LEBS probe, according to one embodiment.

FIG. 7B is a graphical representation of an LEBS probe, according to one embodiment.

Figure 7C:
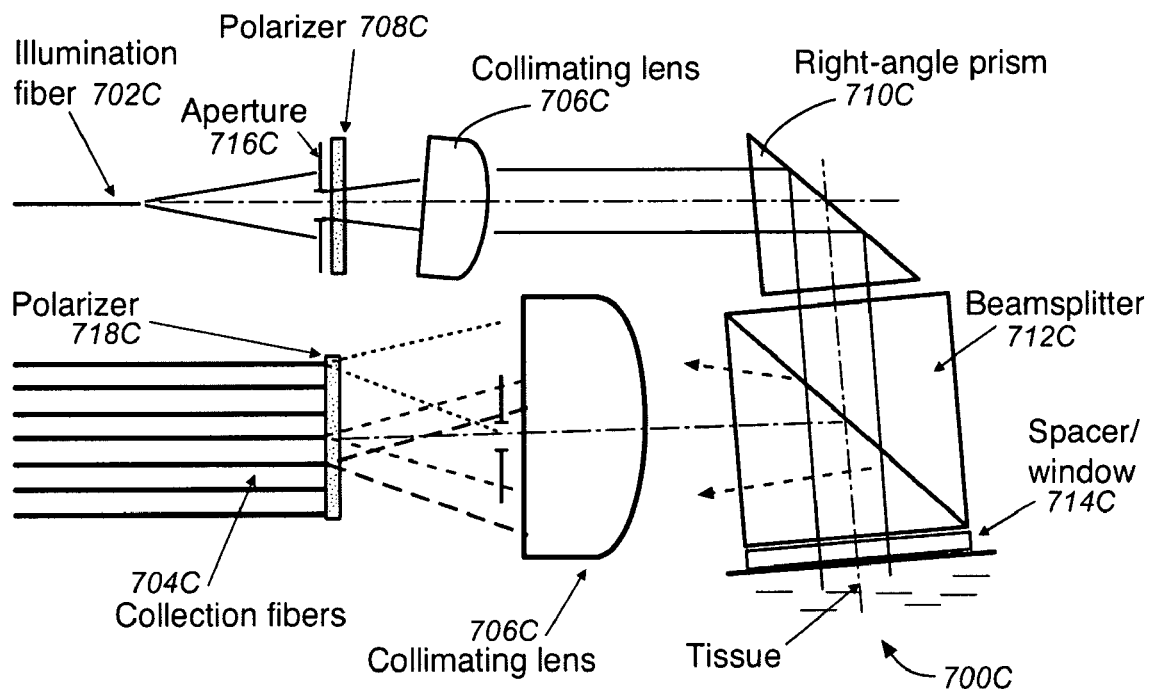
FIG. 7C illustrates a design of a probe having fiber optics for LEBS spectroscopy, according to one embodiment.

FIG. 7C illustrates a design of a probe 700C having fiber optics for LEBS spectroscopy, according to one embodiment.

The probe 700C includes at least one illumination fiber 702C to deliver partially coherent light onto a target object of interest, and at least one collection fiber 704C to collect backscattered light. In one embodiment, the probe 700C also includes a combination of optical components to collimate the incident light. For example, the combination of optical components can be a combination of a lens and an aperture, two lens 4f-system with an aperture position in the common focal plane of the two lenses, etc.

In one embodiment, the probe 700C also includes a collimating lens 706C, a right-angle prism 710C, a beam splitter 712C. Further, the probe may also include a spacer 714C between the beam splitter and a sample stage. The spacer thickness can be varied to adjust the distance between the lens and the sample/tissue surface depending on the measurement characteristics desired such as the depth of tissue to be probed.

In one embodiment, a lens (e.g., positive lens) on the tip of the probe can focus light to a number of light-collecting fibers to transmit this light to a spectrometer grating coupled to an imaging device (e.g., CCD) or a set of photodetectors. In one embodiment, the length of spatial coherence is controlled by at least one of the degree of coherence of light coupled to the delivery fiber, properties of the fiber and the output (e.g., collimating) optics on the fiber tip. For example, the diameter of the at least one delivery optical fiber can be adjusted to determine the spatial coherence of the incident light. Since a larger fiber diameter supports more optical modes, the spatial coherence length of the output light decreases.

In addition, the numerical aperture of the at least one delivery optical fiber can be adjusted to determine the spatial coherence length of the incident light. For example, a larger numerical aperture decreases the spatial coherence length of the light output from the optical fiber.

In one embodiment, light delivery and collection arms of the probe are decoupled. The decoupled delivery and collection arms enables acquisition of light scattered in directions opposite to that of the incident light (e.g., 0° backscattering) in addition to light scattered at larger backscattering angles. In one embodiment, the above mentioned lenses can be any of a Fourier lens, a ball lens, a graded refractive index lens, an aspheric lens, cylindrical lens, convex-convex lens, and plano-convex lens. Lenses other then the above mentioned lenses can also be used.

Figure 7D:
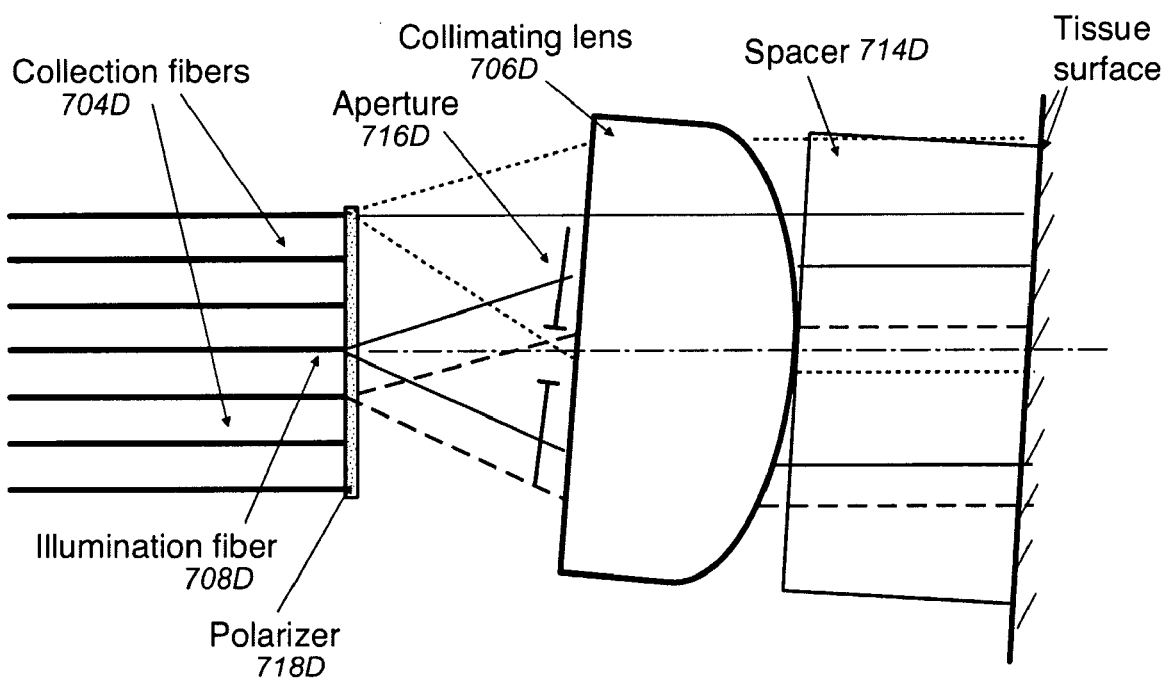
FIG. 7D illustrates a design of a probe having fiber optics for LEBS spectroscopy, according to one embodiment.

FIG. 7D illustrates a design of a probe having fiber optics 700D for LEBS spectroscopy, according to one embodiment.

In one embodiment, the probe 700D includes coupled light delivery 708D and collection arm 704D. Thus, collected light is predominantly from light scattered at larger backscattering angles with smaller contributions from light scattered opposite to that of the incident light (e.g., 0° backscattering). In one embodiment, the probe further includes a lens 706D and an aperture 716D.

Generally, the number of collection optical fibers in the collection arm can vary depending on the comprehensiveness of angular information that is suitable. In one embodiment, there are two collection optical fibers, one corresponding to the tip of LEBS peak (e.g., 0° in the design shown in probe 700B) and the other corresponding to the incoherent baseline (e.g., to collect the backscattered light with an angle of backscattering much greater than the width of an LEBS peak). Thus, the LEBS spectrum can be determined by subtracting properly calibrated baseline signal from that of at the peak of LEBS.

In one embodiment, the probes 700C-D allow collection of spectrum-derived LEBS markers from the depth of LEBS signal penetration including at least one of a spectral slope, correlation decay rate, spectral principal components, and the enhancement factor. In order to vary the depth of penetration, the spatial degree of coherence of the incident light can be changed. In one embodiment, three collection fiber are utilized to measure the width of LEBS peak.

In one embodiment, the number of collection optical fibers can be increased on both sides of the delivery optical fiber to increase the accuracy of measurements by facilitating baseline subtraction and calibration since the angular resolution of the backscattered light is increased. Furthermore, improving the angular resolution of the LEBS profile, a) can enable depth-resolved measurements (the number of different depth probed by the probe is proportional to the number of collecting fiber within the LEBS peak), b) can improve signal-to-noise ratio, and c) can facilitate baseline subtraction.

In one embodiment, the probe can include more than one delivery fiber (e.g., illumination fiber). The more than one delivery fiber can facilitate obtaining optical markers from different regions simultaneously. Each delivery fiber can be coupled to a same set of optical components or different sets of optical components (e.g., lens, aperture, polarizer, etc.).

Figure 7E:
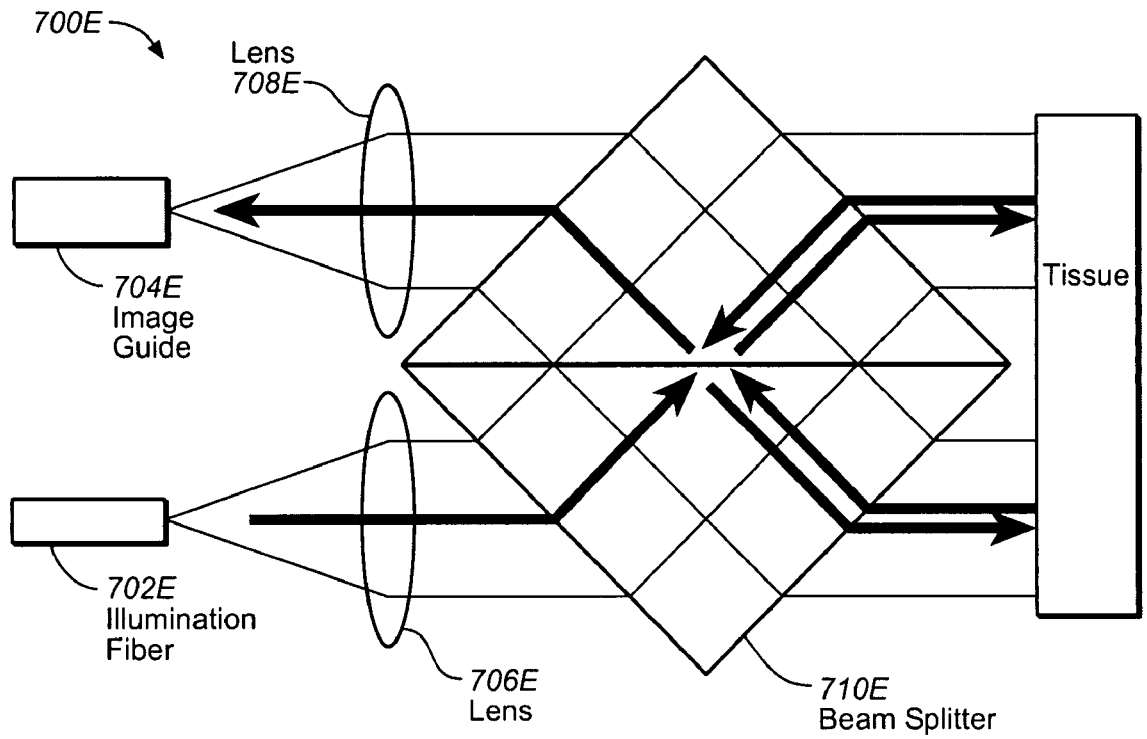
FIG. 7E illustrates a design of a parallel beam probe for LEBS spectroscopy, according to one embodiment.

FIG. 7E illustrates a design of a parallel beam probe for LEBS spectroscopy, according to one embodiment.

In one embodiment, the parallel beam design employs a beam splitter that produces two parallel illumination beams. In the parallel beam probe, Illumination is delivered via optical fibers and collimated with a lens. The collimated beam can then be sent into a cube beam splitter that is approximately parallel to the partially reflective hypotenuse. The beam is incident on the face of the beam splitter at approximately 45 degrees and is refracted towards the hypotenuse where it can be divided into two beams. Further, each beam can be refracted as it exits the beam splitter resulting in two parallel beams located on each side of the hypotenuse.

These beams can both be directed into the tissue. Further, the backscattered light returns through the beam splitter and a portion of each beam is directed out of the cube parallel to the illumination beam on the opposite side of the beam splitter hypotenuse. The backscattered light is then imaged via collection lens.

Figure 7F:
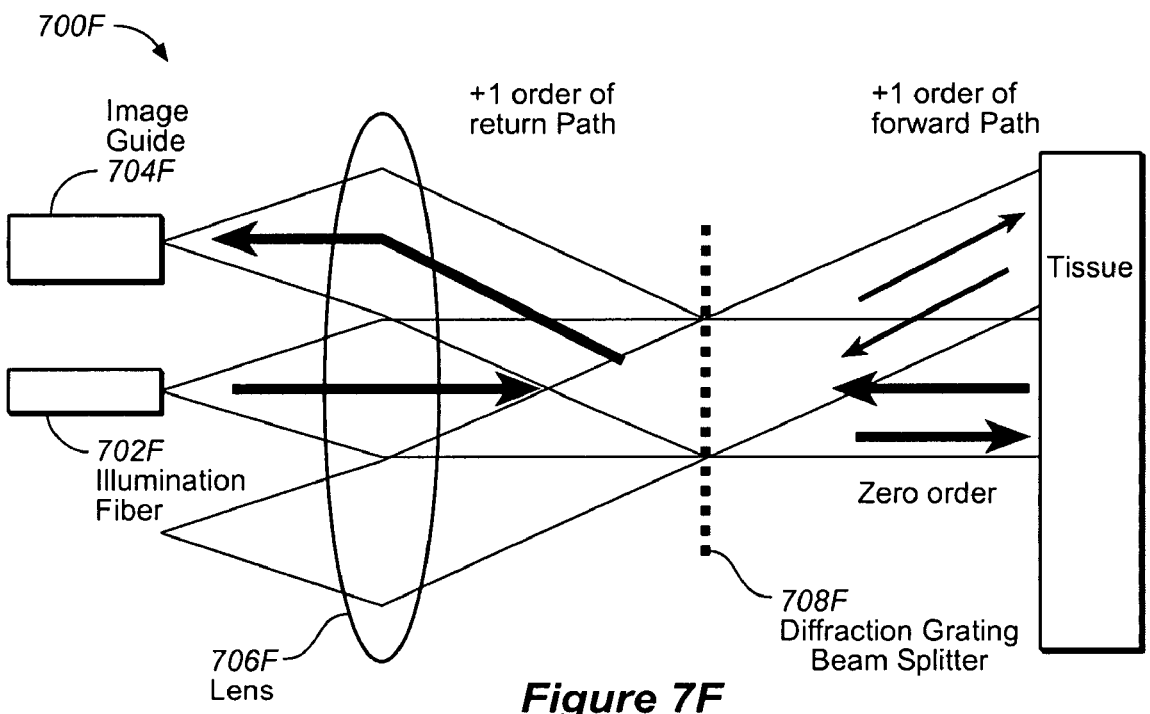
FIG. 7F illustrates a design of a grating beam splitter probe for LEBS spectroscopy, according to one embodiment.

FIG. 7F illustrates a design of a grating beam splitter probe for LEBS spectroscopy, according to one embodiment.

In a diffraction grating based probe, the beam splitter component is replaced with a diffraction grating, in one embodiment. The illumination can be delivered via optical fiber and collimated by a lens. The collimated beam passes through a diffraction grating and is split into two or more diffraction orders. The zero-order light can be projected on the tissue. The backscattered light returns through the grating and is again split. The second pass zero-order returns to the illumination fiber and the first order diffraction exits the grating at a different angle.

In one embodiment, the backscattered light can be collected by the same lens, and focused to a point adjacent to the illumination fiber. The image formed is collected with either a detector or an image guide. In this case, however, the image can be dispersed in one direction according to spectrum and the grating equation. Along one axis of the image, coordinates can correspond to the angle of backscattered light, but along the other image axis, the LEBS peak can be dispersed according to the spectral content. In one embodiment, the dispersed image can be to produce both angular and spectral information directly without utilizing a separate spectrometer. The use of zero-order diffraction for illumination and first-order diffraction for collection is one example of the many geometries possible when using a diffraction grating beam splitter.

Figure 7G:
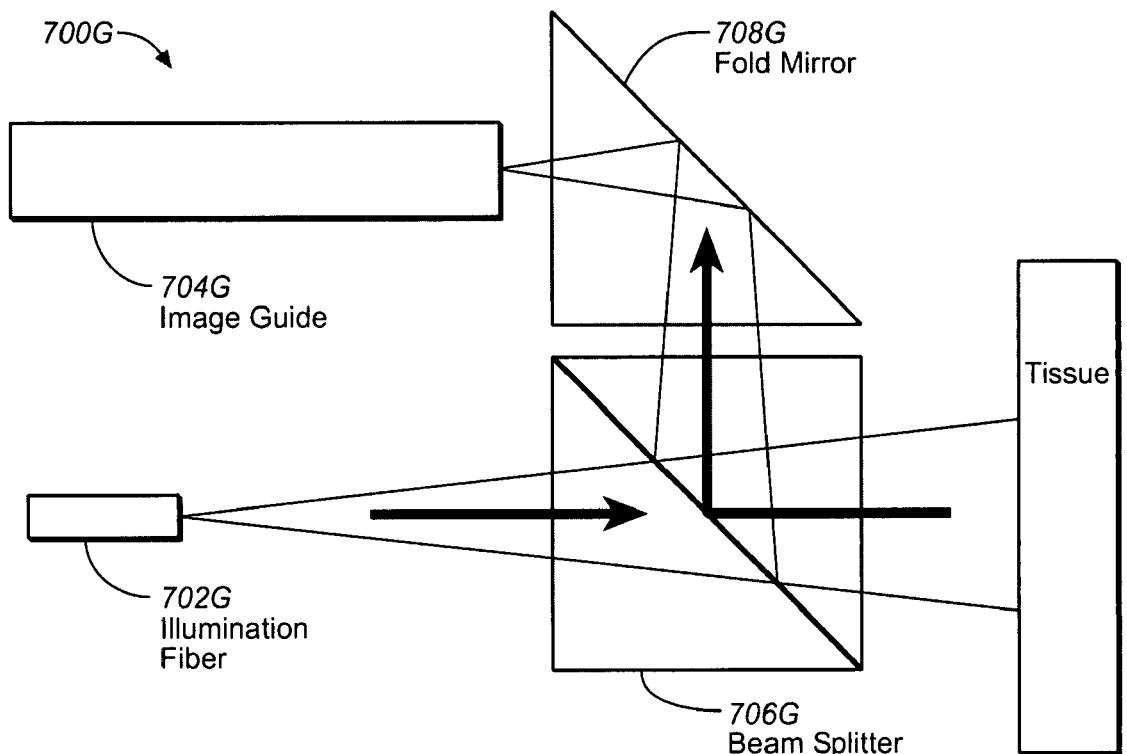
FIG. 7G illustrates a design of a lens-less probe for LEBS spectroscopy, according to one embodiment.

FIG. 7G illustrates a design of a lensless probe for LEBS spectroscopy, according to one embodiment.

The lensless LEBS probe illuminates tissue directly with an optical fiber and collects the backscattered light, in one embodiment. For example, the illumination is not initially collimated (e.g., by a lens) before being projected onto the target object.

In one embodiment, the spatial coherence length can determined by the diameter of the illumination fiber core and the distance from the fiber to the tissue. In the case of collimated illumination, the angle of incidence is approximately constant throughout the illuminated spot. The LEBS peak can be associated with the retroreflected rays that return in small angles about the incident rays. In a lensless geometry, the angle of incidence of illumination is typically not constant over the illumination spot, but in each local region, the retroreflected rays return about a small angle relative to the incident rays for that region.

Therefore, the LEBS peak can be localized in space at a distance from the tissue approximately equal to the illumination distance. In one embodiment, the LEBS image is positioned on a detector or image guide without a collection lens. The illumination fiber can be separated from the LEBS image by use of a beam splitter.

Figure 7H:
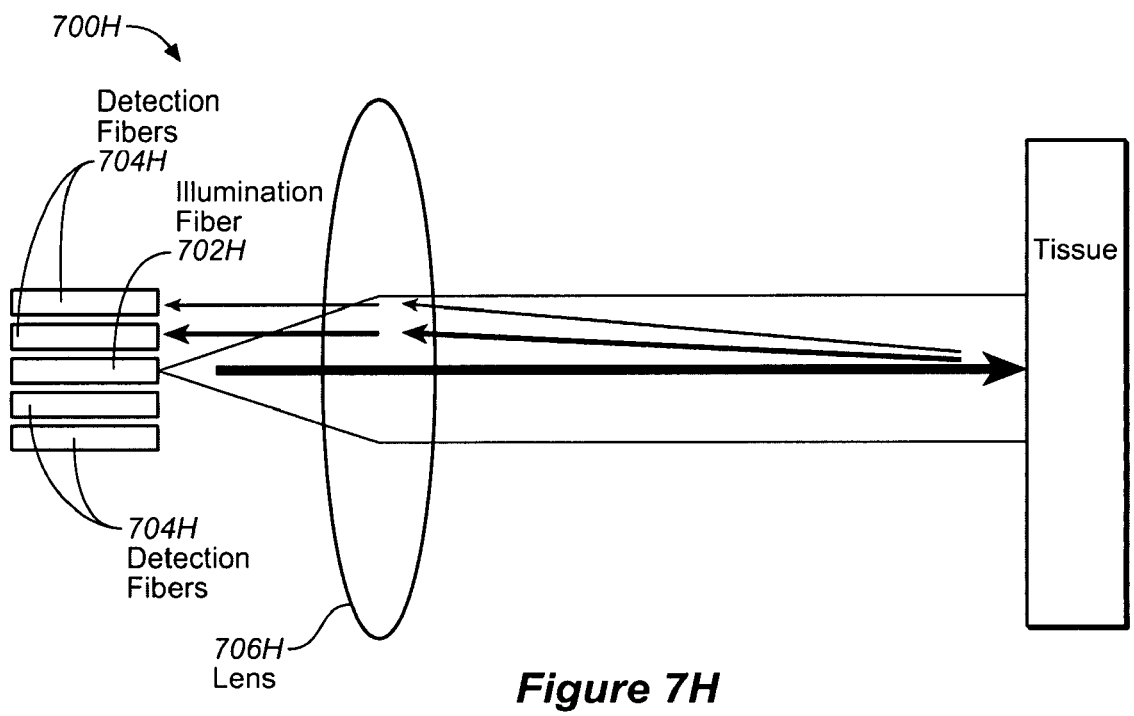
FIG. 7H illustrates a design of an n-fiber probe for LEBS spectroscopy, according to one embodiment.

FIG. 7H illustrates a design of an n-fiber probe for LEBS spectroscopy, according to one embodiment.

A small number of detection fibers are placed adjacent to the illumination fiber and only the side lobes of the LEBS peak are collected, in one embodiment. The illumination is delivered via an optical fiber and collimated by a lens. The collimated beam can illuminate the tissue and the backscattered light is to be focused back onto the illumination fiber. The approximately 0-degree backscattered light can fall on the illumination fiber. In one embodiment, the delivery fiber is used for illumination only and the approximate zero-degree backscattering that falls onto this fiber is not detected, but the adjacent fibers surrounding the illumination fiber detect the side lobe(s) of the LEBS peak. In one embodiment, the illuminating light emerging from a light source is coupled into the delivery fiber through a beam splitter (which may or may not be a part of the probe).

In one embodiment, the beam splitter can be used to divert the zero-degree backscattered light collected by the delivery fiber into the detection arm of the system. Therefore, the tip of the LEBS peak can be collected. In one embodiment, a number of discrete points sample the LEBS peak and incoherent background at predetermined angular positions and are collected to determine one or more optical markers.

System Components

In one embodiment, an apparatus couple-able to a light source and a target object, to facilitate light transmission between the light source to the target object, includes a probe to emit incident light that is partially coherent light obtained from the light source onto the target object and to receive interacted light.

The light source can be a single broadband light source (e.g., an arc lamp that emits white light) with a smooth broad spectrum. Similarly, the light source can also be a white light emitting diode (WLED) to provide broadband illumination. In one embodiment, the light source is a combination of coherent light sources with different wavelengths. For example, the source can be a combination of lasers emitting at different wavelengths for providing effective coupling and high intensity of the incident light. Similarly, the light source may be a combination of LEDs that emit at different wavelengths.

By using semiconductor lighting devices (e.g., LEDs, lasers, etc.), sequential light pulses can be applied to the imaged target object. Different subsets of the LEDs and/or lasers can be switched on based on the desired illumination spectra since different applications may have different suitable illumination spectra due to specific anatomic properties. For example, tissues obtained from different anatomical regions may be more sensitive at different tissue depths. The ability to pulse different subsets of the semiconductor lighting devices (e.g., LED, lasers, etc.) can enable imaging different types of tissues for various applications with one probe.

The interacted light to be backscattered light from illumination of the incident light on the target object. The probe may include a delivery channel having at least one delivery optical fiber with a distal end portion couple-able to the light source and a proximal end portion suited to deliver the incident light to be projected on the target object.

The probe can further include a collection channel having at least one collection optical fiber suited to collect light, the at least one optical fiber having a proximal end portion to receive the light to be backscattered from illumination of the partially coherent light on the target object, and a distal end portion adapted to be coupled to a receiving end, and a plurality of optical components optically coupled to the proximal end portion of one or more of the at least one delivery optical fiber and the at least one collection optical fiber. The collection channel can be implemented with a bundle of fiber to sample a substantial portion of the angular data. This may be the ideal implementation when angular markers are important for analysis. In one embodiment, the collection channel is implemented with a smaller number of collection optical fibers useful when the spectral markers are more prominent.

In one embodiment, one or more of the plurality of optical components are optically coupled to the proximal end portion of the at least one delivery fiber to collimate the incident light. One or more of the plurality of optical components are adjustably positioned at the proximal end portion of the at least one delivery optical fiber to vary the spatial coherence length of the incident light. In one embodiment, the plurality of optical component includes at least one of a lens and an aperture. For example, at least one of the positions of the lens and the aperture are adjustable to vary a spatial coherence length of the partially coherent light to be projected on the target object.

In one embodiment, the plurality of optical components comprises a two lens 4-f system and an aperture disposed substantially in a common focal plane of the two lenses. The lens can be disposed approximately one focal length from the second end of the at least one optical fiber of the delivery channel and the collection channel. Substantially one focal length can be one focal length, greater than one focal length, or less than one focal length.

The plurality of optical components may include a first polarizer optically coupled to one or more of the at least one delivery optical fibers and the at least one collection optical fibers to provide polarization to one or more of the incident light and the interacted light that is to be coupled to the at least one collection optical fibers. The first and second polarizers may be orthogonal to each other. In one embodiment, the first and second polarizers are at angles to each other that are different than 90 degrees and 45 degrees. The polarizers can allow for the adjustment of polarization of at least one of the incident light and the interacted light.

In one embodiment, the lens is to focus the backscattered light on the at least one collection optical fiber based on at least one angular component of backscattering angle of the backscattered light. A second lens may be optically coupled to the proximal end portion of the at least one collection optical fiber to focus the backscattered light on the at least one collection optical fiber based on the at least one angular component of the backscattering angle of the backscattered light. In one embodiment, the proximal end portion of the at least one collection optical fiber is optically coupled to one or more of the lens, the second lens, and a polarizer to project an angular distribution of the backscattered light on the spectrograph.

In one embodiment, the receiving end includes at least one of a spectrograph and a light detector. The spectrograph can be coupled to the light detector (e.g., CCD, photodetector) such that different spectral components of light can be recorded by the light detector thus resulting in a high spectral resolution of the collected optical data.

In one embodiment, the spectral information is acquired via sequential pulsing of the light source rather than the spectrometer. For example, semiconductor light devices (e.g., LED, lasers) can be sequentially pulsed in time at specific wavelengths. Thus, the detector can be gated in time to take snapshots that correspond to the wavelength of light that was pulse at a particular time In one embodiment, the receiving end includes multiple single-channel spectrometers to sample the LEBS spectra at discrete angular components. Each single-channel spectrometer can collect the backscattered light backscattered at a particular angle or a particular range of angles. The angular data to be obtained is based on the number of the channel spectrometers and/or the position of the channel spectrometers. The angle resolution that can be attained is based on the number of channel spectrometers.

In one embodiment, the receiving end includes a filter to sample the LEBS data at different wavelengths. The filter can be one or more of a tunable filter (e.g., accousto-optics), filter wheel, and dichroics. The filters can be used with a CCD (where all angles are measured) and/or a small number of detectors (e.g., photo-detectors, single channel spectrometers) where a discrete sample of angular components are measured.

The probe can include an end that is suited for insertion into a human body. For example, the probe may be adapted to be fitted into a colonoscope, endocscope, or laparoscope channel.

Example Systems

In an LEBS experiment, LEBS peak can be measured as a function of both angle and wavelength. The two dimensional data can be used to calculate LEBS markers or signatures whose numerical values can be used to characterize tissue and provide diagnosis. In some applications, measuring the LEBS signal as a function of both angle and wavelength may not be necessary and only portion of the signal may have to be recorded. Thus, a subset of optical markers can be identified, that is suitable for a particular application.

The optical markers include spectrum-based and angular distribution based. Other markers can be developed too. As discussed, one of the advantages of LEBS is that it allows optical analysis of tissue at different depth from the surface. In a particular application one most diagnostic depth can be chosen or a number of depth may have to be assessed. The penetration depth can be determined by the coherence length of illumination. In addition, a particular penetration depth can be obtained from the angular information.

Therefore, the spectrum-based markers (e.g., spectral slope, autocorrelation decay rate, principal component index) can be assessed for a specific angle of scattering and, thus, can be associated with a penetration depth. In addition, angular distribution based markers may be associated with a particular maximum penetration depth, which in turn can be determined by the illumination. Depending on the configuration of illumination, detection and probe design, different combinations of LEBS markers can be obtained.

In a preferred embodiment when measurements of spectral optical markers are important, the system includes a white LED, an n-fiber probe. The n-fiber probe may or may not have a parallel beam design. On the receiving end, the collection optical fibers are coupled to a linear-array spectrometer.

In one example embodiment, the system includes a white light emitting diode, an n-fiber probe. The receiving end can include a series of tunable filters and intensity detectors with time-sequential acquisition of the signal at different wavelengths. The number of wavelengths acquired can depend on the complexity of the system. In one embodiment, some spectral markers can be obtained with this system.

In another example embodiment, the system includes a color and/or a white LED for illumination, an n-fiber probe, and a number of intensity detectors. The number of intensity detectors may match the number of collection fibers. Optical markers including the enhancement factor and the peak width can be collected.

Carcinogen-Treated Animal Model

Animal models can be valuable in understanding pathophysiologic mechanisms and can be used for the development of diagnostic biomarkers and treatment strategies. In particular, animal models are useful for studying the early stages of carcinogenesis. Therefore, animal studies are conducted with carcinogen-treated rats to test the potential of LEBS spectroscopy for the diagnosis of early precancerous changes in the colon.

For example, the AOM-treated rat model has been used for studying colon carcinogenesis and developing diagnostic biomarkers and chemopreventive agents. The AOM-treated rat model is a suitable animal model of colon carcinogenesis because of the similarities in the morphological, genetic, and epigenetic alterations with human colon carcinogenesis.

Figure 8:
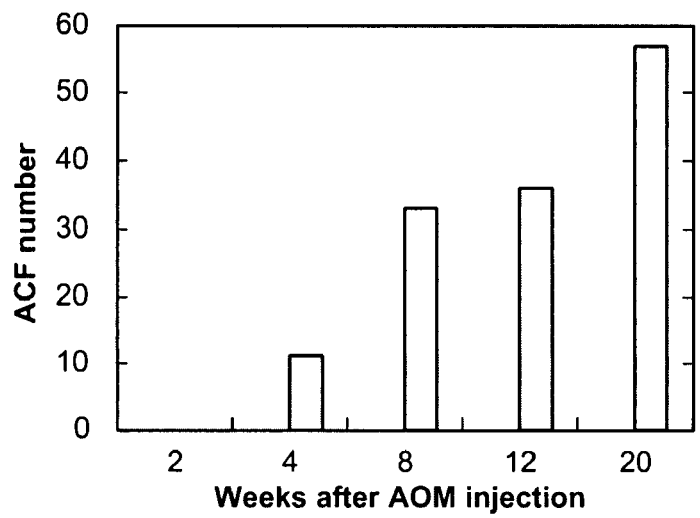
FIG. 8 illustrates progression of one of the first marker of colon carcinogensis, aberrant crypt foci (ACF) in azoxymethane-treated (AOM-treated) rats, according to one embodiment.

FIG. 8 illustrates progression of one of the first marker of colon carcinogensis, aberrant crypt foci (ACF) in azoxymethane-treated (AOM-treated) rats, according to one embodiment.

As can be seen, LEBS signatures change noticeably and can be used as accurate biomarkers of colonic preneoplasia as early as 2 weeks after AOM injection.

Figure 9:
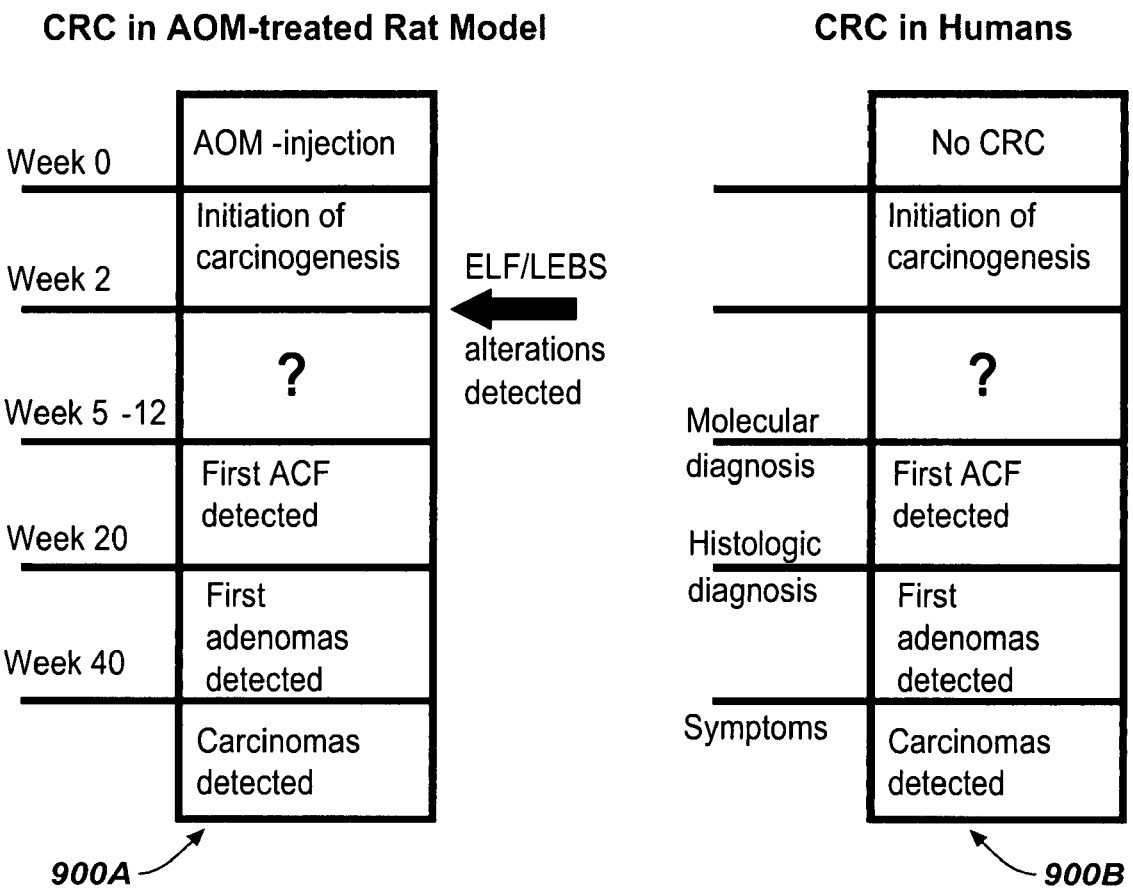
FIG. 9 illustrates the time course of colon carcinogenesis progression in the AOM-treated rat model and that in humans, according to one embodiment.

FIG. 9 illustrates the time course of colon carcinogenesis progression in the AOM-treated rat model 900A and that in humans 900B, according to one embodiment.

In azoxymethane (AOM)-treated rats, colon carcinogenesis progresses through similar steps as in humans. For example, the earliest detectable marker of colon carcinogenesis, aberrant crypt foci, are precursor lesions which are observed on the colonic mucosal surface in both the AOM-treated rat model and in humans. In AOM-treated rats, aberrant crypt foci develop in ~8-12 weeks after the AOM injection, adenoma or carcinomas can be observed in 20-30 weeks, and carcinomas develop after 40 weeks.

As in human colon carcinogenesis, end-stage lesions (e.g., tumors, 40 weeks after AOM injection) may be symptomatic. Earlier lesions (e.g., adenoma or carcinomas, >20 weeks post AOM treatment) may not lead to symptoms but can be detected histologically by means of microscopic examination of biopsy. Thus, the science of molecular biology may push the frontiers of cancer detection even earlier: Aberrant crypt foci can be detected as early as approximately 8 weeks after AOM treatment. However, no histological, molecular or genetic, markers have so far been discovered to allow diagnosis earlier than 4-12 weeks after the initiation of carcinogenesis.

Rats (e.g., Fisher rats) were randomized equally to groups that received either two weekly intraperitoneal injections of AOM (e.g., 15 mg/kg) or saline. Rats were fed standard chow and sacrificed at various time points after the second injection. Colons of the rats were removed, flushed with phosphate buffered saline, and immediately exposed to LEBS analysis to ensure that optical measurements were performed on fresh tissue.

Figure 10:
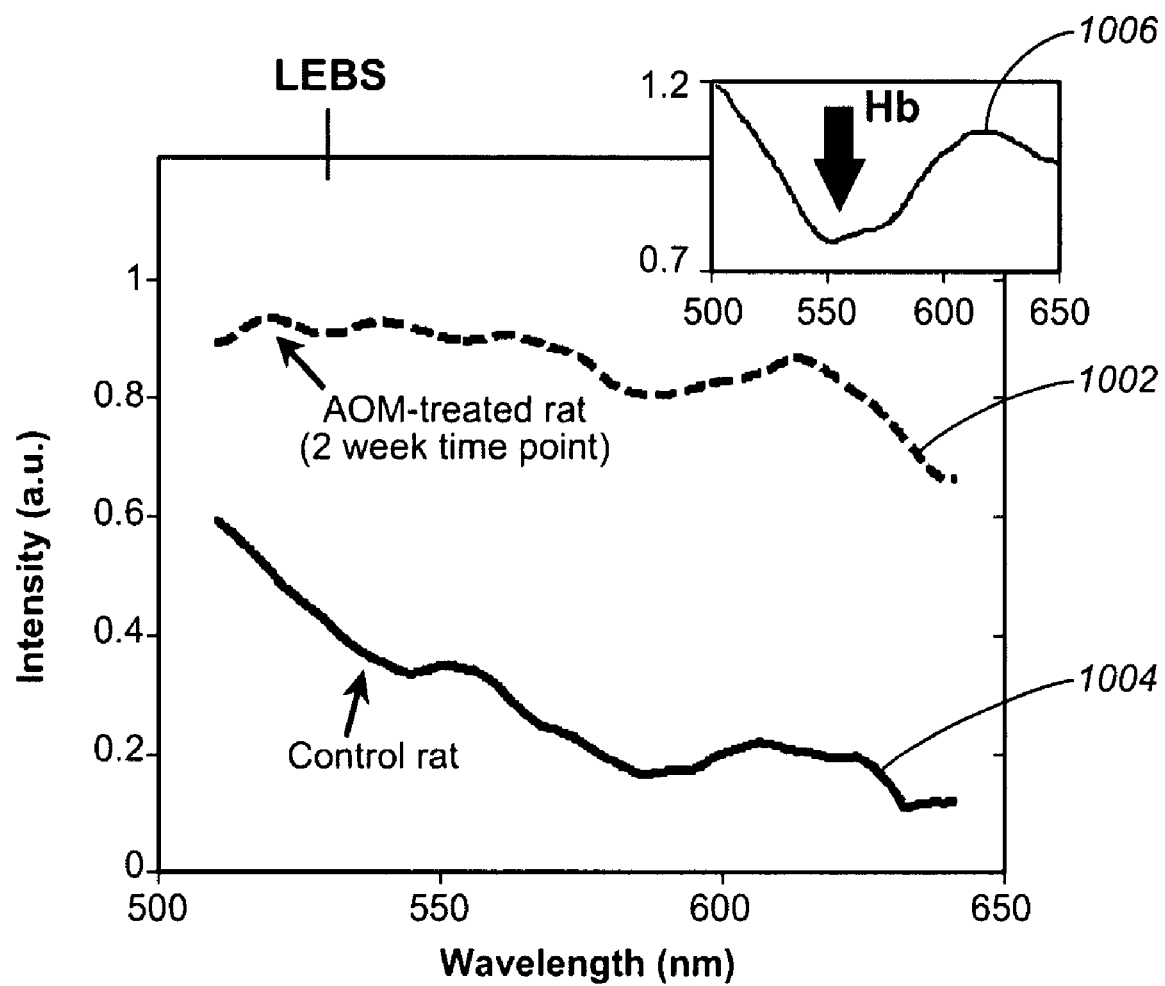
FIG. 10 is an intensity plot of the spectral distribution of LEBS (backscattered) signals recorded from histologically normal tissue in the AOM-treated rat model, according to one embodiment.

FIG. 10 is an intensity plot of the spectral distribution of LEBS (backscattered) signals recorded from histologically normal tissue in the AOM-treated rat model, according to one embodiment.

The spectra was recorded from rat colons of azoxymethane-treated rats at an early, pre-ACF stage of carcinogenesis 1002 (e.g., 2 weeks after azoxymethane treatment), and age-matched control animal 1004 (saline treatment). The inset 1006 illustrates a diffuse reflectance spectrum recorded from the same tissue site (AOM-treated rat) affected by Hb-absorption obscuring endogenous spectral signatures of the epithelium. For comparison, LEBS spectra is not affected by Hb-absorption.

The LEBS spectra $I_{EBS}(k)$ can be obtained from $I_{EBS}(\theta,k)$ by integrating over the backscattering angle $\theta$. As shown, the LEBS spectra obtained from the preneoplastic and control colonic tissues are noticeably different. Thus, quantitative analysis of such LEBS spectra can reveal a number of highly significant spectral markers that were diagnostic for the earliest field changes in colon carcinogenesis.

Figure 11:
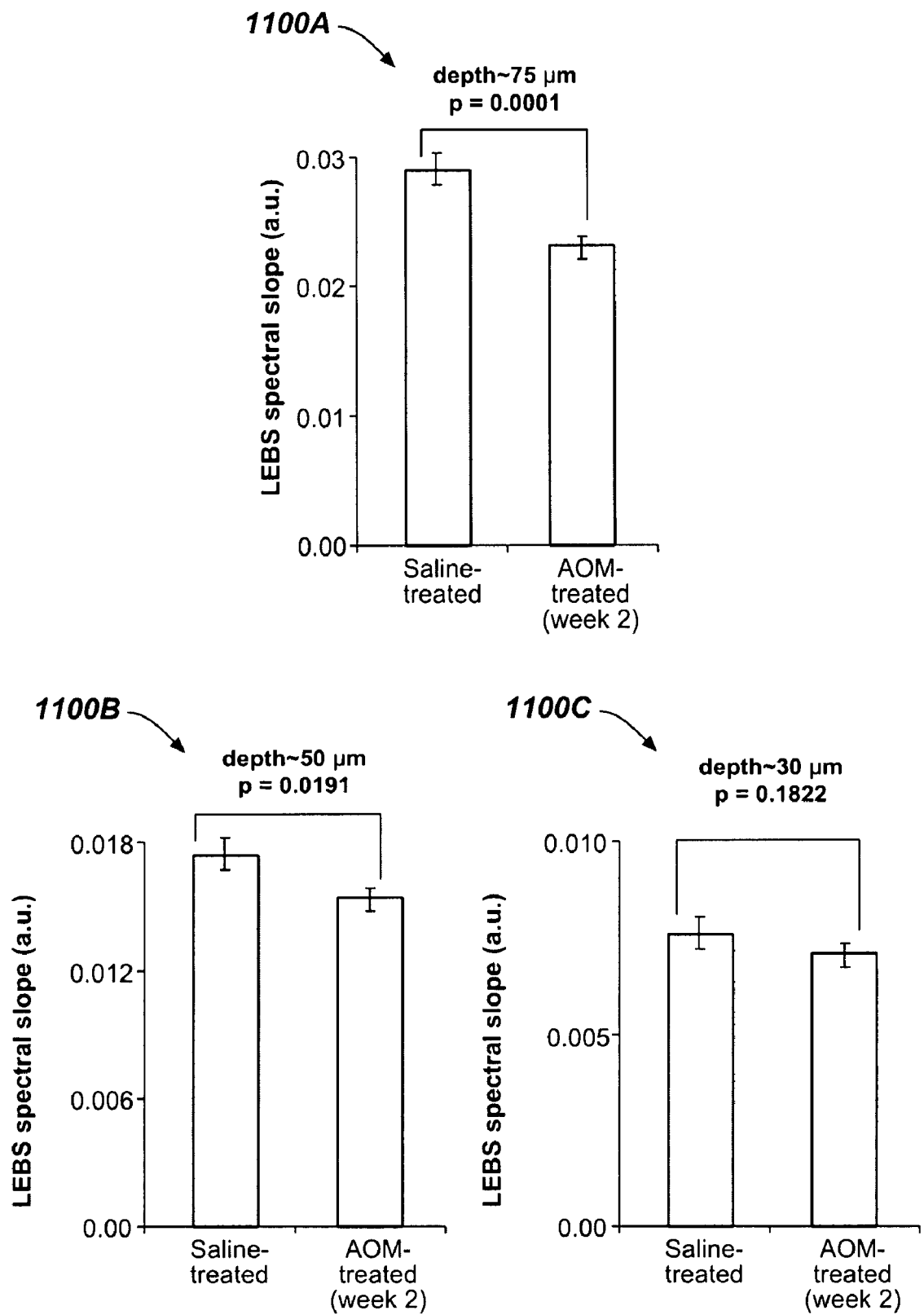
FIG. 11 is set of bar diagrams comparing the spectral slopes of LEBS signals obtained from rat colonic tissues approximately 2 weeks after azoxymethane (AOM) administration and the saline-treated rats of tissues obtained at different locations in the colon, according to one embodiment.

FIG. 11 is set of bar diagrams comparing the spectral slopes of LEBS signals obtained from rat colonic tissues approximately 2 weeks after azoxymethane (AOM) administration and the saline-treated rats of tissues obtained at different locations in the colon, according to one embodiment.

The results from tissue obtained in the lower compartment (~75 μm) are illustrated in plot 1100A. The results obtained near the center of the compartment (~50 μm) are illustrated in plot 1100B. The results obtained in the upper compartment (~30 μm) of the colonic mucosa are illustrated in plot 1100C.

The optimal depth of penetration for which LEBS markers are more diagnostic can be determined. Because the scattering angles determine the depth of penetration, a series of angles that corresponded to 30, 50, and 75 μm depths (e.g., angles ~0.4 degrees, ~0.2 degrees, and ~0 degrees, respectively) were evaluated to obtain depth selective measurements.

One pre-ACF time point in the azoxymethane-treated rat model (e.g., 2 weeks after azoxymethane administration) was selected. LEBS signals $I_{EBS}(\lambda,k)$ were recorded from at least 20 tissue sites per animal equally distributed throughout colonic surface. LEBS spectra $I_{EBS}(k)$ were calculated from these signals as previously discussed above for each tissue depth. As shown, signals recorded from 75-μm depth yielded larger distinction than the 30, and 50 μm depths between the control and azoxymethane-treated rats. Signals were not recorded from deeper depths given that the signals recorded from deeper tissue are potentially affected by hemoglobin absorption. In the following animal studies, LEBS spectra were analyze from tissue obtained from around this critical depth.

Figure 12A:
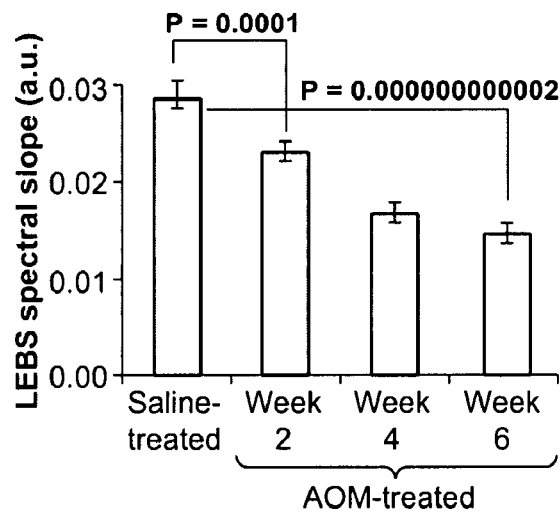
FIG. 12A is a bar diagram illustrating changes in the LEBS spectral slope obtained from rat colonic tissues approximately 2, 4, and 6 weeks after azoxymethane (AOM) administration compared with the saline-treated rats, according to one embodiment.

FIG. 12A is a bar diagram illustrating changes in the LEBS spectral slope obtained from rat colonic tissues approximately 2, 4, and 6 weeks after azoxymethane (AOM) administration compared with the saline-treated rats, according to one embodiment.

Because the carcinogenic effects of azoxymethane progress over time, for LEBS signals serving as an intermediate biomarker, it is expected the magnitude of alterations of LEBS markers to increase over time. The LEBS spectral slope progressively decreased at these early stages (2, 4, or 6 weeks after carcinogen injection). In the azoxymethane-treated rats, the LEBS spectral slope was observed to be decreased as early as 2 weeks after the carcinogen treatment ($P<0.00001$) and continued to decrease over the course of the experiment ($P<0.0001$).

Figure 12B:
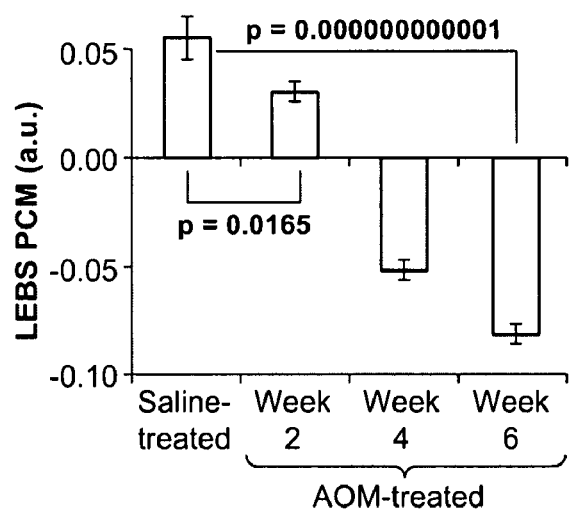
FIG. 12B is a bar diagram illustrating changes in the LEBS principal component marker (PCM) obtained from rat colonic tissues approximately 2, 4, and 6 weeks after azoxymethane (AOM) administration compared with the saline-treated rats, according to one embodiment.

FIG. 12B is a bar diagram illustrating changes in the LEBS principal component marker (PCM) obtained from rat colonic tissues approximately 2, 4, and 6 weeks after azoxymethane (AOM) administration compared with the saline-treated rats, according to one embodiment.

The statistically significant alteration of the LEBS spectral slope serves as a strong argument for the neoplastic relevance of this LEBS marker. However, spectral slope harnesses a proportion of LEBS information. To more fully appreciate the complexity of the information contained in LEBS spectra, principal component analysis was also performed on the LEBS data.

First, the principal component of interest was determined and the results indicated that in the tissue data, the first two principal components (PC1 and PC2) accounted for 99% of the data variance. The diagnostic principal components as a linear combination of PC1 and PC2 and identified principal component marker=PC1+5PC2 was determined to be the significant combination.

Therefore, LEBS principal component marker can be used as a convenient means to characterize the light scattering data. It was shown that LEBS principal component marker was significantly decreased at the 2-week time point ($P<0.02$) and continued to progressively decrease over the course of the experiment ($P<0.000001$), following the temporal progression of carcinogenesis.

LEBS Markers in the MIN Mouse

Although the azoxymethane-treated rat model has been well validated, to ensure that the changes in LEBS signatures are not model specific, similar experiments were performed in an alternate model of intestinal carcinogenesis, the MIN mouse.

The MIN mouse is a genetic model with a germ line mutation in the APC where the initiating mutation in most sporadic colon carcinogenesis. The MIN mouse has been observed to spontaneously develop intestinal adenoma or carcinomas starting at ages 9 to 10 weeks. The LEBS signatures obtained from the MIN mice were compared with age-matched negative control C57BI mice. The control C57BI mice differ from the MIN mice in that they harbor a wild-type APC gene.

For the animal subjects (e.g., MIN mice and control mice), LEBS data were recorded for a number of tissue sites spaced uniformly across the surface of the small bowel. It was determined that the LEBS markers that were significant for early colon carcinogenesis in the azoxymethane-treated rats were also diagnostic for the early preadenoma or carcinoma stage of intestinal neoplasia in the approximately 6-week-old MIN mice. Specifically, the intestinal mucosa was investigated at approximately week 6 when the mucosa is histologically normal.

Figure 13A:
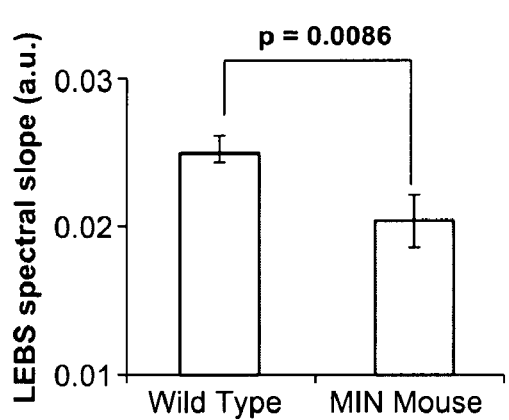
FIG. 13A is a bar diagram illustrating changes in the LEBS spectral slope recorded from the uninvolved MIN mouse mucosa (distal small bowel) in the 6-week-old MIN mouse compared with age-matched mice that were wild type for APC loci, according to one embodiment.

FIG. 13A is a bar diagram illustrating changes in the LEBS spectral slope recorded from the uninvolved MIN mouse mucosa (distal small bowel) in the 6-week-old MIN mouse compared with age-matched mice that were wild type for APC loci, according to one embodiment.

Figure 13B:
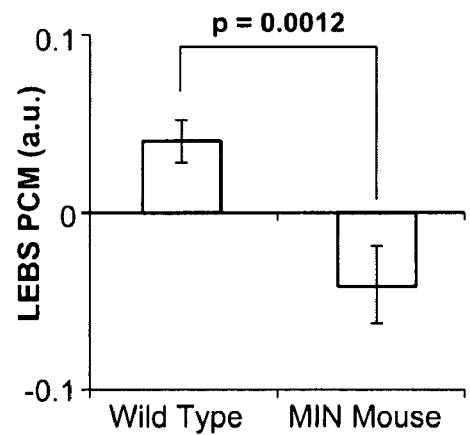
FIG. 13B is a bar diagram illustrating changes in the LEBS principal component marker (PCM) recorded from the uninvolved MIN mouse mucosa (distal small bowel) as being altered in the 6-week-old MIN mouse when compared with age-matched mice that were wild type for APC loci, according to one embodiment.

FIG. 13B is a bar diagram illustrating changes in the LEBS principal component marker (PCM) recorded from the uninvolved MIN mouse mucosa (distal small bowel) as being altered in the 6-week-old MIN mouse when compared with age-matched mice that were wild type for APC loci, according to one embodiment.

As shown in FIG. 13A-B, at this pre-neoplastic time point, there were dramatic alterations in both the LEBS spectral slope (e.g., P<0.01) and LEBS principal component marker (e.g., P<0.01).

Pilot Human Data

Human study was conducted by assessing LEBS spectral slope using ex vivo tissue obtained from human subjects undergoing colonoscopy. In this experiment, a low-risk group is defined as those without personal history of neoplasia (e.g., from both current and previous colonoscopies) and no family history of adenomas/carcinomas. Twenty patients were noted to have adenoma or carcinomas on current colonoscopy, and these lesions were relatively uniformly distributed between the right and left colon. The detected adenoma or carcinomas were histologically confirmed.

The LEBS data were obtained from endoscopically normal rectum tissue, mid-transverse colon, and the cecum at a predetermined distance (e.g., at least 5 cm.) away from any neoplastic lesion. In addition, LEBS data can also be obtained from tissue of the ascending colon, hepatic flexure, transverse colon, splenic flexure, descending colon, and/or sigmoid colon to detect adenoma or carcinoma in the colon.

Figure 14A:
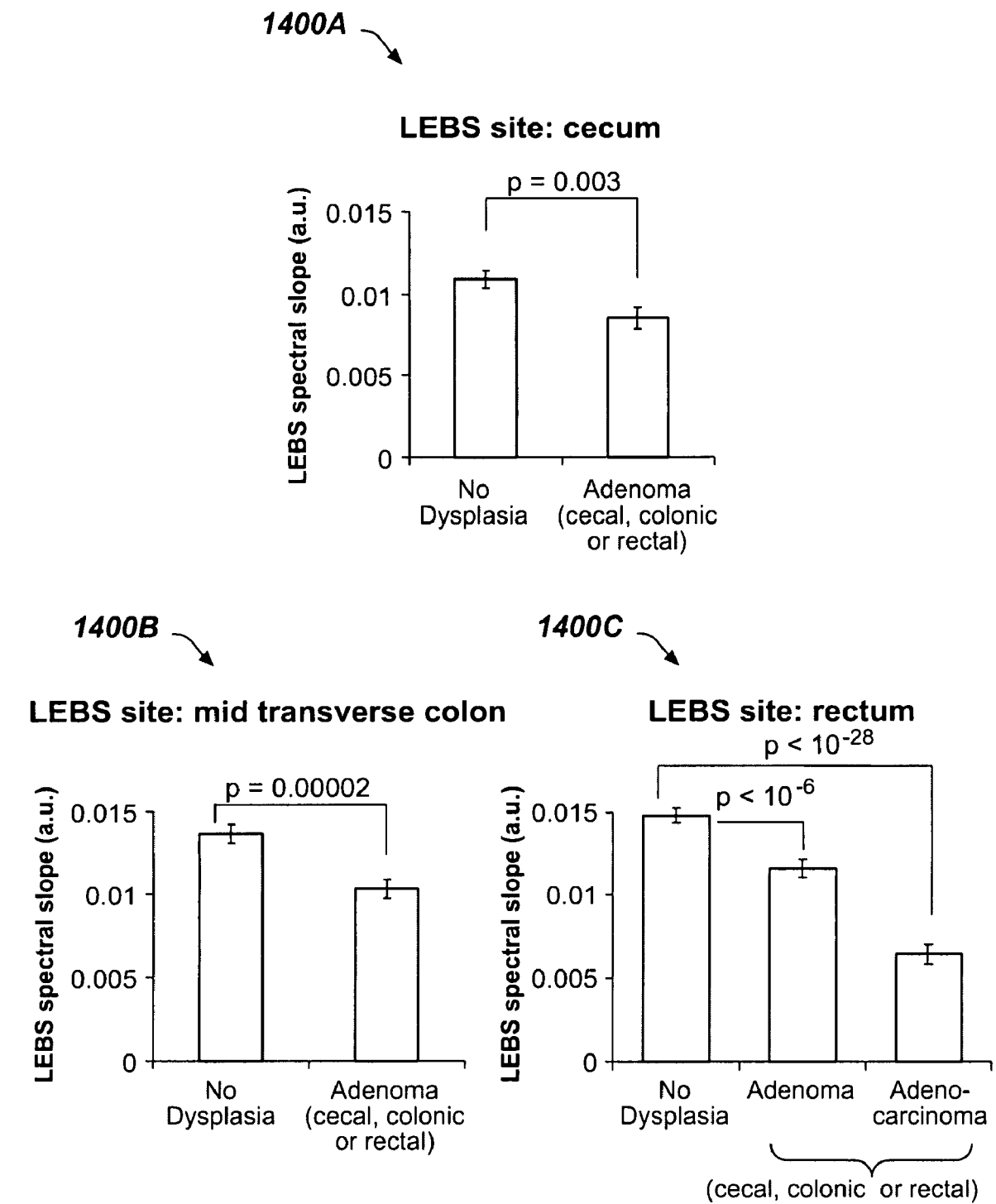
FIG. 14A is a set of bar diagrams illustrating data obtained from human studies where LEBS spectral slopes were assessed from colonoscopically normal mucosa in the cecum, the midtransverse colon, and the rectum of subjects undergoing colonoscopy, according to one embodiment.

FIG. 14A is a set of bar diagrams illustrating data obtained from human studies where LEBS spectral slopes were assessed from colonoscopically normal mucosa in the cecum 1400A, the midtransverse colon 1400B, and the rectum 1400C of subjects undergoing colonoscopy, according to one embodiment.

As can be seen, the spectral slope in cancer patients was decreased even more significantly than in patients with adenoma or carcinomas. By performing LEBS, a significant decrease in the spectral slope obtained from the three segments in patients who harbored adenoma or carcinomas somewhere in their colon can be observed when compared with those who were neoplasia free (P<0.01). The magnitude of decrease of spectral slope can be greater if the lesion was located in the same region as the LEBS analysis; however, significant differences were noted from LEBS measurements taken at each of the three colonic segments in patients who harbored adenoma or carcinomas elsewhere in their colon compared to the patients who were neoplasia free (e.g., rectal LEBS spectral slope correlates with the presence of adenoma or carcinomas in the transverse colon).

The decrease of the spectral slope was consistent with a similar alteration of this marker in the azoxymethane treated rat and MIN mouse models. Thus, alteration of light scattering; thus, nanoarchitectural/microarchitectural signatures in the uninvolved mucosa in humans (i.e., the field effect) can be detectable by LEBS. These results demonstrate that LEBS spectroscopy has the potential to accurately risk stratify patients for CRC and may be translated into a practical clinical method for colon cancer screening.

FIG. 14B is a set of bar diagrams illustrating the decay length obtained from the intensity of the LEBS backscattered light from the endoscopically and histologically normal mucosa of the rectum, according to one embodiment.

Autocorrelation of LEBS spectra $C_A(\Delta k)=\int I_{EBS}(k)I_{EBS}(k+\Delta k)dk$, where k is the wave number, indicates the degree of refractive index fluctuations in tissue microarchitecture. It is determined that $C_A$ follows exponential dependence on $\Delta k^2$, $C_A(\Delta k)\propto\exp(-\Delta k^2 D)$, with a high precision (e.g., $R^2=0.98$). The exponential behavior of $C_A$ is characteristic of many random mesoscopic systems where D is referred to as the decay rate.[77] $D\propto(\delta n^2 L_C/L_t)^{-1}\lambda^2$, where $\delta n^2$ is the variance of the refractive index fluctuations within colonic mucosal tissue, $L_C$ is the refractive index correlation length, and $L_t$ is the temporal coherence length of illumination.

In addition, D is sensitive to arbitrary small length scales of refractive index fluctuations and, thus, concentration of tissue solids (up to 1 nm, as confirmed by our numerical FDTD experiments). It is determined that D can be significantly increased at 4 weeks time point (p-value<$10^{-5}$) and continued to progressively increase following the progression of carcinogenesis (p-value<0.01) This indicates progressive increase in tissue inhomogeneity in carcinogenesis.

FIG. 14C is a bar diagram illustrating the full-width at half-maximum (FWHM) of an angular width of LEBS intensity plot obtained from the endoscopically and histologically normal mucosa of the rectum, according to one embodiment.

It can be observed that the angular width of the LEBS peak can be decreased in patients with adenoma or carcinomas.

Figure 15:
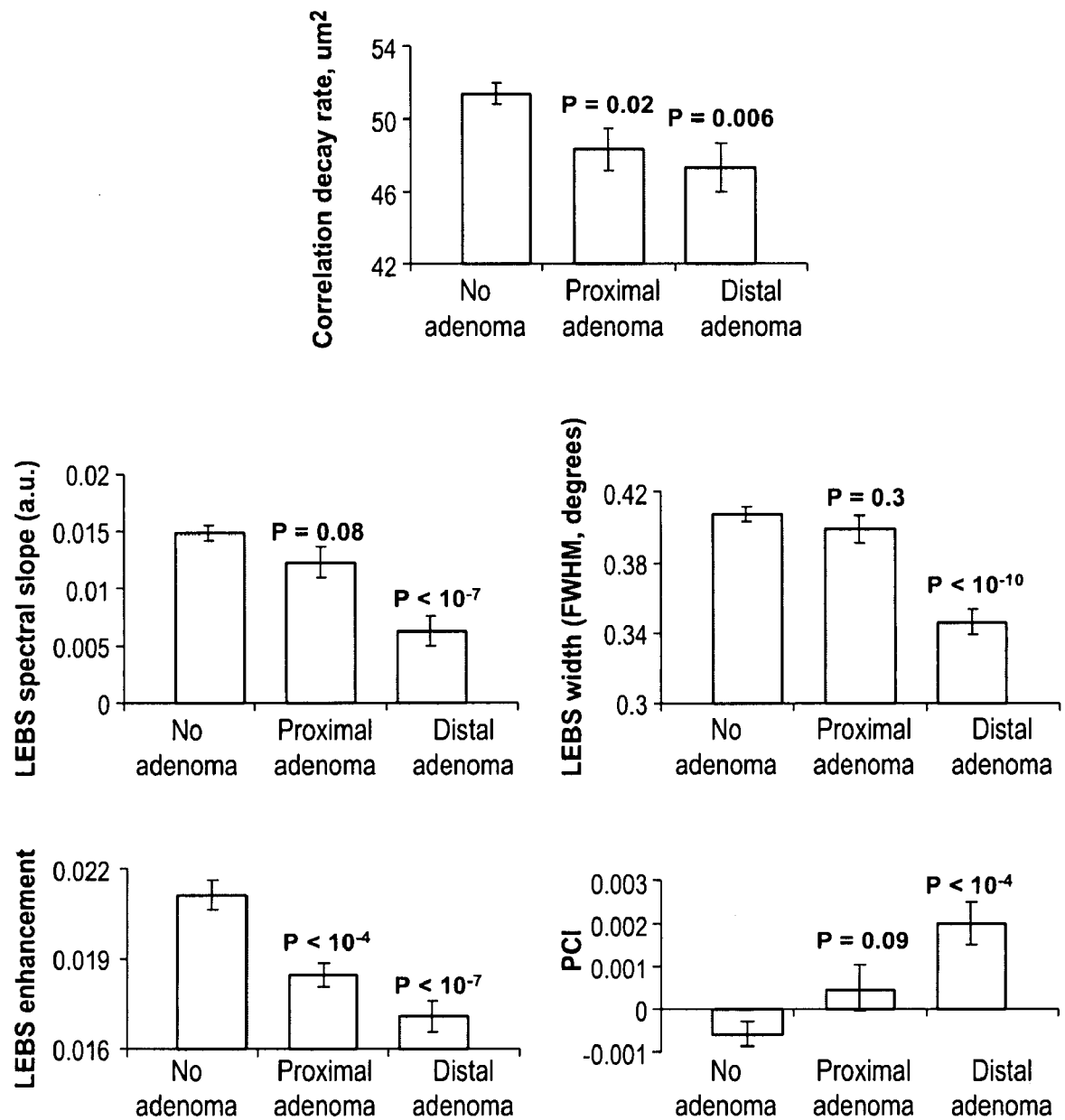
FIG. 15 is a set of bar diagrams illustrating multiple LEBS markers obtained from the rectum from patients with no adenoma, proximal adenoma, or distal adenoma, according to one embodiment.

FIG. 15 is a set of bar diagrams illustrating multiple LEBS markers obtained from the rectum from patients with no adenoma or carcinoma, proximal adenoma or carcinoma, or distal adenoma or carcinoma, according to one embodiment.

As shown, the alteration of LEBS markers (e.g., spectral slope, LEBS enhancement, correlation decay rate, LEBS backscattering peak width, and principal component analysis, etc.) in the rectum was observed not only for distal adenoma or carcinomas (e.g., rectum and sigmoid colon) but also for proximal lesions as well (e.g., transverse and ascending colonic segments). In the data shown in FIG. 14B, the number of patients without adenoma or carcinomas was n=105, patients with adenoma or carcinomas in the distal colon n=21, and patients with adenoma or carcinomas in the proximal colon n=23.

The magnitude of the alteration of the optical markers was less pronounced for proximal adenoma or carcinomas— likely due to increased distance between these adenoma or carcinomas and the rectum. For instance, while six markers were significant for distal adenoma or carcinomas, two markers were significant for proximal adenoma or carcinomas and two were less significant (p<0.1). Higher p-values for proximal adenoma or carcinomas may in part be due to smaller number of samples (e.g., smaller n).

Thus, in one embodiment, the presence of adenoma or carcinomas in any part of the colon can lead to optically detectable changes in tissue throughout the colon. Further, the decreased alteration of LEBS markers with distance from an adenoma or carcinoma correlates with that LEBS can detect field effect changes due to the development of an adenoma or carcinoma.

Performance Characteristics of LEBS Markers

FIG. 16 is a table of calculated sensitivity and specificity of LEBS markers for predicting neoplastic risk, derived from the rat, mice, and human data, according to one embodiment.

The performance characteristics were calculated for AOM-treated rats (compared with age-matched, saline-treated controls) at pre-ACF (e.g., 2 weeks) and preadenoma or carcinoma (e.g., 6 weeks) time points. The MIN mouse data were obtained at a preadenoma or carcinoma time point (e.g., week 6). The human data were obtained from endoscopically normal mucosa at least a predetermined amount of distance (e.g., 5 cm.) away from any neoplastic lesion and correlated with advanced adenoma or carcinoma occurrence elsewhere in the colon.

As shown in the table, the performance characteristics of LEBS markers in the azoxymethane-treated rat were high at the pre-ACF phase (week 2) and approximately 100% at a later stage (week 6), when ACF may occur but before adenoma or carcinoma development. Similar results were noted in the pre-neoplastic MIN mouse mucosa. Finally, clinical data suggests that rectal LEBS had high sensitivity and specificity for the presence colonic of advanced adenoma or carcinomas (≧1 cm, villous features or high-grade dysplasia).

It was also determined that the magnitude of alterations in LEBS markers (e.g., LEBS spectral slope) was greater in patients with more advanced lesions compared with simple adenoma or carcinomas (data not shown).

LEBS Markers are Not Compromised by Confounding Factors

Patient Age

FIG. 17 is a table showing results of correlation analysis between a patient's age and an LEBS marker, according to one embodiment.

Given that the age is a major risk factor for CRC, in order to ensure that the changes in LEBS detect carcinogenesis as opposed to age difference between patients with adenoma or carcinomas and control subjects, the variation of LEBS markers with age is determined via experiment.

To further address the effect of age, two types of analyses were performed: 1) the two-factor ANOVA, which is a conventional method to determine if age influences the markers and 2) correlation analysis, where each individual optical markers was correlated with age. In the two-factor ANOVA, patients were dichotomized based on their age as being younger or older than 60 years old. As shown in the table, both types of analysis indicated that none of the six markers changed significantly with age. Thus, it is highly unlikely that the changes in the optical signatures are due to the age differences in the patient population.

Further Applications of LEBS (1) Detection of early, previously undetectable stages of precancerous lesions in endoscopically or laparoscopically accessible organs, such as colon, esophagus, stomach, bladder, oral cavity, cervix, ovary, etc. This can be achieved by means of LEBS-guided colonoscopy.

(2) Screening or risk-stratification of patients for colorectal cancer (CRC) screening. As our data indicate, EBS has the potential to identify precancerous alterations in colon tissue far earlier than other currently known markers of colon carcinogenesis. If a colon tissue is accessed by means EBS, only four readings would provide a 99% probability of correctly detecting abnormal signatures even at previously undetectable stages of carcinogenesis. Thus EBS may be used to identify patients at increased risk of CRC and in the need of colonoscopy or treatment, such as chemoprevention. Not only does LEBS enable CRC detection at an early stage, it also enables the diagnosis of the presence of precancerous lesions (e.g. adenoma or carcinomas) by assessment of endoscopically and histologically normal-appearing tissue at a distance from a lesion. In particular, it has been demonstrated that LEBS assessment of rectal tissue alone (which can be easily accessed without the need for colonoscopy) reliably predicts the presence of adenoma or carcinomas anywhere else in the colon.

(3) Screening for pancreatic cancer. Pancreatic cancer is the fifth leading cause of cancer death in the United States with most cancers diagnosed at a late, incurable stage. Most of the existing approaches, including high-resolution imaging (MRI, CT, etc.), molecular diagnostics, and endoscopic cholangiopancreatography (ERCP), has not shown the capability to detect pancreatic neoplasms sufficiently early to allow effective treatment. Current imaging modalities as well as ERCP depend on the presence of a mass lesion, and, therefore, even if the resolution of these tests is improved, we will still be dealing with a tumor that is biologically too advanced for cure. Despite years of research no clinically adequate molecular markers have been developed. The only route that currently has the potential for diagnosing pre-invasive cancer is through the pancreatic duct, where 90% of adenocarcinomas of the pancreas originate. Due to the potential for complications including pancreatitis (3-5% cases), as currently performed, ERCP is not suitable for routine screening over successive points in time.

Given that the region around the ampulla of Vater is exposed to the same environmental and genetic milieu as the pancreatic duct, it is biologically plausible that the field effect should extend to this region of the small bowel. This opens up a possibility to diagnose pancreatic neoplasia by means of examination of duodenal and ampullar tissue in the vicinity of the pancreatic duct, which can be readily accomplished by means of existing upper-endoscopic techniques without the risk of pancreatitis or other serious complications.

A study has been initiated to explore the feasibility of detection of pancreatic neoplasms by means of spectroscopic assessment of a portion of duodenum and ampulla of Vater adjacent to the pancreatic duct and without the need to interrogate the pancreatic duct itself. The data involving 51 human subjects demonstrate that duodenal LEBS measurements enable detection of pancreatic early cancerous lesions (e.g. stage 1) with 96% sensitivity and 91% specificity.

(4) Monitoring of efficacy of chemoprevention and other anticancer strategies in humans. The ability to detect changes associated with the action of chemo-preventive agents is crucial for the development of effective anticancer strategies. A myriad of agents have demonstrated chemo-preventive efficacy in experimental systems. However, clinical studies remain difficult and expensive because of the insufficiency of existing intermediate biomarkers for early carcinogenesis and chemoprevention and, therefore, the long follow up needed to demonstrate the protective effects of agents. Thus, finding an easily detectable, sensitive, and accurate intermediate biomarker for colon carcinogenesis would be beneficial in designing chemo-preventive strategies. Ideally, such biomarker would quantitatively assess the efficacy of a chemo-preventive strategy early in the course of the therapy, which is of great benefit to patients undergoing the therapy, drug developers developing or evaluating the agent, and biomedical researchers investigating the mechanisms of carcinogenesis and chemoprevention. With unprecedented sensitivity and non-invasiveness, EBS may potentially become an ideal tool for monitoring of chemoprevention.

(5) Monitoring of efficacy of chemoprevention and other anticancer strategies in experimental models of CRC. Most cancer-prevention or treatment agents are first investigated in animal models, such as AOM-treated rat model discussed above. However, in this and similar models tumorigenesis is a long process. For example, in AOM-treated rat model, which is one of the most frequently used model of CRC, it takes more than 40 weeks for colon tumors to develop. This limits how fast the efficacy of a therapeutic or cancer-preventive agent can be tested in a pharmaceutical company or a research lab. As indicated by our results, LEBS may significantly decrease the time necessary to test experimental agents in animal models by sensing very early changes induced by the agent (within a few weeks instead of several months). This may potentially result in reduction of time necessary to develop and test anticancer agents.

(6) Monitoring bioengineered tissue during development, growth, and/or interaction with other tissues.

(7) Monitoring of the fabrication of elastomeric scaffolds, non-invasive measurement of the properties of the elastomeric scaffolds. For example, to assess the viability and the interaction with host tissue. A typical citric acid-based elastomer is poly(1,8 octanediol-co-citric acid) (POC). Another elastomer also under study is poly(glycerol sebacate) (PGS). LEBS can be used to characterize both POC and PGS elastomers as well as polystyrene of various molecular weights. As mechanical properties depend on the ultrastructure and chemical make up of a material, obtaining information pertinent to the degree of crosslinking (i.e. molecular weight between cross-links) should give insight into the mechanical properties of the material (i.e. Young's Modulus, tensile strength).

(8) Monitoring of the fabrication of polymers and non-invasive measurement of the properties of the polymers and the non-invasive measurements. For example, the slope of the intensity versus wavelength spectra wave can be determined to obtain correlation to mechanical and molecular weight data. The size distribution of the scattering structures can be correlated to mechanical and molecular weight data. There are intrinsic structural characteristics of polymers that can be correlated to the extent of reaction and mechanical properties. LEBS can detect morphological structures in solid polymeric materials which can be used to assess the extent of reaction and mechanical characteristics. The correlation between spectral slope and the log of molecular weight between cross links, Young's modulus and tensile strength, and the log of molecular weight can be determined.

(9) Assessment of various properties (e.g., size and granules) of the power materials such as dies.

(10) Monitoring the growth and development of human aortic smooth muscle cells. For example, the size distributions can be obtained from SMCs grown on laminin and fibornectin.

(11) Optical characterization of solid polymeric materials to determine the structural information. LEBS can be suitable for mechanical properties and molecular weight characterization of linear polymers.

Although embodiments have been described with reference to specific exemplary embodiments, it will be evident that the various modification and changes can be made to these embodiments. Accordingly, the specification and drawings are to be regarded in an illustrative sense rather than in a restrictive sense. The foregoing specification provides a description with reference to specific exemplary embodiments. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A method for measuring the properties of a target object, comprising:
   providing incident light comprising at least one spectral component having low coherence, wherein the incident light is to be illuminated on a target object in vivo;
   recording an intensity of one or more of at least one spectral component and at least one angular component of backscattering angle of backscattered light, wherein the backscattered light is to be backscattered from illumination of the incident light on the target object and wherein the backscattering angle is an angle between the direction of incident light propagation and the direction of backscattered light propagation;
   analyzing the intensity of the one or more of the at least one spectral component and the at least one backscattering angle of backscattered light to obtain one or more optical markers of the backscattered light, toward evaluating said properties; and
   adjusting a spatial coherence length of the incident light to select a depth of penetration of the target object by the incident light.

2. The method of claim 1, wherein the backscattered light is low coherence enhanced backscattered light.

3. The method of claim 1, wherein the optical marker is at least one of a spectral marker and an angular marker.

4. A method for measuring the properties of a target object, comprising:
   providing incident light comprising at least one spectral component having low coherence, wherein the incident light is to be illuminated on a target object in vivo;
   recording an intensity of one or more of at least one spectral component and at least one angular component of backscattering angle of backscattered light, wherein the backscattered light is to be backscattered from illumination of the incident light on the target object and wherein the backscattering angle is an angle between the direction of incident light propagation and the direction of backscattered light propagation; and
   analyzing the intensity of the one or more of the at least one spectral component and the at least one backscattering angle of backscattered light to obtain one or more optical markers of the backscattered light, toward evaluating said properties;
   wherein the optical marker is at least one of a spectral marker and an angular marker, and wherein the angular marker is a decay rate of a Fourier transform of the intensity of the at least one angular component of the backscattered light with respect to an independent Fourier variable of the Fourier transform.

5. A method for measuring the properties of a target object, comprising:
providing incident light comprising at least one spectral component having low coherence, wherein the incident light is to be illuminated on a target object in vivo;
recording an intensity of one or more of at least one spectral component and at least one angular component of backscattering angle of backscattered light, wherein the backscattered light is to be backscattered from illumination of the incident light on the target object and wherein the backscattering angle is an angle between the direction of incident light propagation and the direction of backscattered light propagation; and
analyzing the intensity of the one or more of the at least one spectral component and the at least one backscattering angle of backscattered light to obtain one or more optical markers of the backscattered light, toward evaluating said properties;
wherein the optical marker is at least one of a spectral marker and an angular marker, and wherein the angular marker is at least one of an angular width, a correlation decay rate, and an enhancement factor of the intensity of the at least one angular component of the backscattered light.

6. A method for measuring the properties of a target object, comprising:
providing incident light comprising at least one spectral component having low coherence, wherein the incident light is to be illuminated on a target object in vivo;
recording an intensity of one or more of at least one spectral component and at least one angular component of backscattering angle of backscattered light, wherein the backscattered light is to be backscattered from illumination of the incident light on the target object and wherein the backscattering angle is an angle between the direction of incident light propagation and the direction of backscattered light propagation; and
analyzing the intensity of the one or more of the at least one spectral component and the at least one backscattering angle of backscattered light to obtain one or more optical markers of the backscattered light, toward evaluating said properties;
wherein the optical marker is at least one of a spectral marker and an angular marker, and wherein the spectral marker is one or more of a spectral slope, a spectral exponential, a correlation decay rate, and at least one principal component of the intensity of the at least one spectral component of the backscattered light.

7. The method of claim 4, further comprising adjusting a spatial coherence length of the incident light to select a depth of penetration of the target object by the incident light.

8. The method of claim 1, wherein the recording comprises recording a matrix of intensities of backscattered light as a function of wavelength and backscattering angle.

9. The method of claim 1, wherein the target object is one of at least a portion of the living subject or a biological sample.

10. The method of claim 1, further comprising obtaining the optical marker from tissue of an anatomical region proximal to tissue of the anatomical region potentially harboring neoplasia.

11. The method of claim 10, further comprising detecting presence of neoplasia in at least a part of a human organ via detecting optical changes via at least one optical marker from tissue to be obtained from anywhere in said organ or a surrogate site in another organ the colon.

12. The method of claim 1, wherein the incident light is provided by a probe.

13. The method of claim 12, wherein the probe comprises at least one delivery optical fiber.

14. The method of claim 13, wherein the delivery optical fiber comprises a distal end portion suited to be coupled to a light source and a proximal end portion suited to deliver the incident light to be projected on the target object.

15. The method of claim 13, wherein the probe further comprises a polarizer optically coupled to one or more of the at least one delivery optical fibers to provide polarization to the incident light.

16. The method of claim 12, wherein the probe includes an end suited for insertion into a human body, via one of direct insertion or an endoscopic device.

17. The method of claim 1, wherein the backscattered light is collected by a probe.

18. The method of claim 17, wherein the probe comprises at least one collection optical fiber suited to collect light.

19. The method of claim 18, wherein the at least one optical fiber comprises a proximal end portion to receive the light to be backscattered from illumination of the incident light on the target object, and a distal end portion adapted to be coupled to a receiving end.

20. The method of claim 18, wherein the probe further comprises a polarizer optically coupled to one or more of the at least one collection optical fibers to provide polarization to the backscattered light.

21. The method of claim 18, wherein the probe further comprises a lens to focus the backscattered light on the at least one collection optical fibers.

22. The method of claim 21, wherein the lens focuses the backscattered light based on at least one angular component of backscattering angle of the backscattered light.

23. The method of claim 17, wherein the probe includes an end suited for insertion into a human body, via one of direct insertion or an endoscopic device.

* * * * *

UNITED STATES PATENT AND TRADEMARK OFFICE
CERTIFICATE OF CORRECTION

PATENT NO. : 7,652,772 B2 Page 1 of 1
APPLICATION NO. : 11/803029
DATED : January 26, 2010
INVENTOR(S) : Vadim Backman et al.

It is certified that error appears in the above-identified patent and that said Letters Patent is hereby corrected as shown below:

Replace the text found in column 1, line 66 through column 2, line 5, with the following text:

-- This invention was made with government support under Grant No. 1R01CA112315 and Grant No. U01CA111257 awarded by the National Institutes of Health and BES-0238903 awarded by the National Science Foundation. The government has certain rights in the invention. --

Signed and Sealed this

Fifth Day of October, 2010

David J. Kappos
*Director of the United States Patent and Trademark Office*